United States Patent [19]

Canich

[11] Patent Number: 5,096,867

[45] Date of Patent: * Mar. 17, 1992

[54] MONOCYCLOPENTADIENYL TRANSITION METAL OLEFIN POLYMERIZATION CATALYSTS

[75] Inventor: Jo Ann M. Canich, Webster, Tex.

[73] Assignee: Exxon Chemical Patents Inc., Linden, N.J.

[*] Notice: The portion of the term of this patent subsequent to Oct. 8, 2008 has been disclaimed.

[21] Appl. No.: 581,841

[22] Filed: Sep. 13, 1990

Related U.S. Application Data

[63] Continuation-in-part of Ser. No. 533,245, Jun. 4, 1990, Pat. No. 5,055,438, which is a continuation-in-part of Ser. No. 406,945, Sep. 13, 1989, abandoned.

[51] Int. Cl.⁵ .............................................. C08F 4/64
[52] U.S. Cl. .................................... 502/103; 502/117; 502/121; 502/122; 502/123; 502/124; 502/125; 556/11; 526/160
[58] Field of Search ............... 502/103, 117, 121, 122, 502/123, 124, 125

[56] References Cited

FOREIGN PATENT DOCUMENTS

WO87/03887  7/1987  PCT Int'l Appl. ................. 502/117

Primary Examiner—Patrick P. Garvin
Attorney, Agent, or Firm—Jaimes Sher; Myron B. Kurtzman

[57] ABSTRACT

The invention is a catalyst system including a Group IV B transition metal component and an alumoxane component which may be employed to polymerize olefins to produce a high molecular weight polymer.

7 Claims, No Drawings

MONOCYCLOPENTADIENYL TRANSITION METAL OLEFIN POLYMERIZATION CATALYSTS

This application is a continuation-in-part of U.S. Patent Application Ser. No. 533,245 filed June 4, 1990 and now U.S. Pat. No. 5,055,435 which in turn is a continuation-in part of U.S. Patent Application Ser. No. 406,945 filed September 13, 1989 and now abandoned.

FIELD OF THE INVENTION

This invention relates to certain monocyclopentadienyl metal compounds of a Group IV B transition metal of the Periodic Table of Elements, to a catalyst system comprising a monocyclopentadienyl Group IV B transition metal compound and an alumoxane, and to a process using such catalyst system for the production of polyolefins, particularly polyethylene, polypropylene and α-olefin copolymers of ethylene and propylene having a high molecular weight. The catalyst system is highly active at low ratios of aluminum to the Group IV B transition metal, hence catalyzes the production of a polyolefin product containing low levels of catalyst metal residue. Titanium species of the catalyst are stable at high pressures in unsupported form, unlike their bis-cyclopentadienyl titanium compound counterparts, and exhibit the ability to catalyze the incorporation of higher α-olefin comonomer contents for production of higher molecular weight α-olefin copolymers than analogous zirconium and hafnium species of a monocyclopentadienyl transition metal compound.

BACKGROUND OF THE INVENTION

As is well known, various processes and catalysts exist for the homopolymerization or copolymerization of olefins. For many applications it is of primary importance for a polyolefin to have a high weight average molecular weight while having a relatively narrow molecular weight distribution. A high weight average molecular weight, when accompanied by a narrow molecular weight distribution, provides a polyolefin with high strength properties.

Traditional Ziegler-Natta catalyst systems—a transition metal compound cocatalyzed by an aluminum alkyl—are capable of producing polyolefins having a high molecular weight but a broad molecular weight distribution.

More recently a catalyst system has been developed wherein the transition metal compound has two or more cyclopentadienyl ring ligands—such transition metal compound being referred to as a metallocene—which catalyzes the production of olefin monomers to polyolefins. Accordingly, metallocene compounds of a Group IV B metal, particularly, titanocenes and zirconocenes, have been utilized as the transition metal component in such "metallocene" containing catalyst system for the production of polyolefins and ethylene-α-olefin copolymers. When such metallocenes are cocatalyzed with an aluminum alkyl—as is the case with a traditional type Ziegler-Natta catalyst system—the catalytic activity of such metallocene catalyst system is generally too low to be of any commercial interest.

It has since become known that such metallocenes may be cocatalyzed with an alumoxane—rather than an aluminum alkyl—to provide a metallocene catalyst system of high activity for the production of polyolefins.

The zirconium metallocene species, as cocatalyzed or activated with an alumoxane, are commonly more active than their hafnium or titanium analogues for the polymerization of ethylene alone or together with an α-olefin comonomer. When employed in a non-supported form—i.e., as a homogeneous or soluble catalyst system—to obtain a satisfactory rate of productivity even with the most active zirconium species of metallocene typically requires the use of a quantity of alumoxane activator sufficient to provide an aluminum atom to transition metal atom ratio (Al:TM) of at least greater than 500:1 often greater than 5000:1, and frequently on the order of 10,000:1. Such quantities of alumoxane impart to a polymer produced with such catalyst system an undesirable content of catalyst metal residue, i.e., an undesirable "ash" content (the nonvolatile metal content). In high pressure polymerization procedures using soluble catalyst systems wherein the reactor pressure exceeds about 500 bar and reactor temperature exceeds 100° C. only the zirconium or hafnium species of metallocenes may be used. Titanium species of metallocenes are generally unstable at such high pressures and temperatures unless deposited upon a catalyst support.

A wide variety of Group IV B transition metal compounds have been named as possible candidates for an alumoxane cocatalyzed catalyst system. Although bis(cyclopentadienyl) Group IV B transition metal compounds have been the most preferred and heavily investigated for use in alumoxane activated catalyst systems for polyolefin production, suggestions have appeared that mono and tris(cyclopentadienyl) transition metal compounds may also be useful. See, for example U.S. Pat. Nos. 4,522,982; 4,530,914 and 4,701,431. Such mono(cyclopentadienyl) transition metal compounds as have heretofore been suggested as candidates for an alumoxane activated catalyst system are mono(cyclopentadienyl) transition metal trihalides and trialkyls.

More recently, International Publication No. WO 87/03887 describes the use of a composition comprising a transition metal coordinated to at least one cyclopentadienyl and at least one heteroatom ligand as a transition metal component for use in an alumoxane activated catalyst system for α-olefin polymerization. The composition is broadly defined as a transition metal, preferably of Group IV B of the Periodic Table, which is coordinated with at least one cyclopentadienyl ligand and one to three heteroatom ligands, the balance of the transition metal coordination requirement being satisfied with cyclopentadienyl or hydrocarbyl ligands. Catalyst systems described by this reference are illustrated solely with reference to transition metal compounds which are metallocenes, i.e., bis(cyclopentadienyl) Group IV B transition metal compounds.

Even more recently, at the Third Chemical Congress of North American held in Toronto, Canada in June 1988, John Bercaw reported upon efforts to use a compound of a Group III B transition metal coordinated to a single cyclopentadienyl heteroatom bridged ligand as a catalyst system for the polymerization of olefins. Although some catalytic activity was observed under the conditions employed, the degree of activity and the properties observed in the resulting polymer product were discouraging of a belief that such monocyclopentadienyl transition metal compound could be usefully employed for commercial polymerization processes.

A need still exists for discovering catalyst systems that permit the production of higher molecular weight polyolefins and desirably with a narrow molecular weight distribution. It is further desirable that a catalyst be discovered which, within reasonable ranges of ethylene to α-olefin monomer ratios, will catalyze the incorporation of higher contents of α-olefin comonomers in the production of ethylene-α-olefins copolymers.

SUMMARY OF THE INVENTION

The catalyst system of this invention comprises a transition metal component from Group IV B of the Periodic Table of the Elements (*CRC Handbook of Chemistry and Physics*, 68th ed. 1987–1988) and an alumoxane component which may be employed in solution, slurry or bulk phase polymerization procedure to produce a polyolefin of high weight average molecular weight and relatively narrow molecular weight distribution.

The "Group IV B transition metal component" of the catalyst system is represented by the formula:

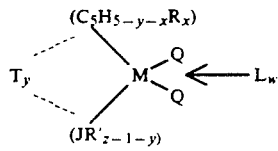

wherein:

M is Zr, Hf or Ti in its highest formal oxidation state (+4, $d^0$ complex);

$(C_2H_{5-y-x}R_x)$ is a cyclopentadienyl ring which is substituted with from zero to five substituent groups R, "x" is 0, 2, 3, 4 or 5 denoting the degree of substitution, and each substituent group R is, independently, a radical selected from a group consisting of $C_1$–$C_{20}$ hydrocarbyl radicals, substituted $C_1$–$C_{20}$ hydrocarbyl radicals wherein one or more hydrogen atoms is replaced by a halogen radical, an amid radical, a phosphido radical, or alkoxy radical, an alkylborido radical or any other radical containing a Lewis acidic or basic functionality, $C_1$–$C_{20}$ hydrocarbyl-substituted metalloid radicals wherein the metalloid is selected from the Group IV A of the Periodic Table of Elements; halogen radicals amido radicals, phosphido radicals, alkoxy radicals, alkylborido radicals or any other radical containing Lewis acidic or basic functionality; or $(C_5H_{5-y-x}R_x)$ is a cyclopentadienyl ring in which at least two adjacent R-groups are joined forming a $C_4$–$C_{20}$ ring to give a saturated or unsaturated polycyclic cyclopentadienyl ligand such as indenyl, tetrahydroindenyl, fluorenyl or octahydrofluorenyl;

$(JR'_{z-1-y})$ is a heteroatom ligand in which J is an element with a coordination number of three from Group V A or an element with a coordination number of two from Group VI A of the Periodic Table of Elements, preferably nitrogen, phosphorus, oxygen or sulfur, and each R' is, independently a radical selected from a group consisting of $C_1$–$C_{20}$ hydrocarbyl radicals, substituted $C_1$–$C_{20}$ hydrocarbyl radicals wherein one or more hydrogen atoms are replaced by a halogen radical, an amido radical, a phosphido radical, an alkoxy radical, an alkylborido radical or any other radical containing a Lewis acidic or basic functionality, and "z" is the coordination number of the element J;

each Q may be independently any univalent anionic ligand such as a halide, hydride, or substituted or unsubstituted $C_1$–$C_{20}$ hydrocarbyl, alkoxide, aryloxide, amide, arylamide, phosphide or arylphosphide, provided that where any Q is a hydrocarbyl such Q is different from $(C_5H_{5-y-x}R_x)$, or both Q together may be an alkylidene or a cyclometallated hydrocarbyl or any other divalent anionic chelating ligand;

"y" is 0 or 1 when w is greater than 0; y is 1 when w is 0; when "y" is 1, T is a covalent bridging group containing a Group IV A or V A element such as, but not limited to, a dialkyl, alkylaryl or diaryl silicon or germanium radical, alkyl or aryl phosphine or amine radical, or a hydrocarbyl radical such as methylene, ethylene and the like;

L is a neutral Lewis base such as diethylether, tetraethylammonium chloride, tetrahydrofuran, dimethylaniline, aniline, trimethylphosphine, n-butylamine, and the like; and "w" is a number from 0 to 3. L can also be a second transition metal compound of the same type such that the two metal centers M and M' are bridged by Q and Q', wherein M' has the same meaning as M and Q' has the same meaning as Q. Such dimeric compounds are represented by the formula:

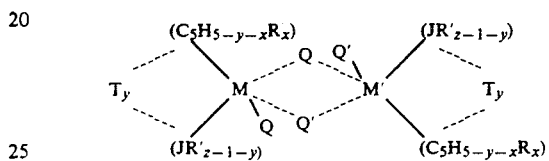

The alumoxane component of the catalyst may be represented by the formulas: $(R^3\text{-Al-O})_m$; $R^4(R^5\text{-Al-O})_m\text{-AlR}^6$ or mixtures thereof, wherein $R^3$–$R^6$ are, independently, a $C_1$–$C_5$ alkyl group or halide and "m" is an integer ranging from 1 to about 50 and preferably is from about 13 to about 25.

Catalyst systems of the invention may be prepared by placing the "Group IV B transition metal component" and the alumoxane component in common solution in a normally liquid alkane or aromatic solvent, which solvent is preferably suitable for use as a polymerization diluent for the liquid phase polymerization of an olefin monomer.

Those species of the Group IV B transition metal component wherein the metal is titanium have been found to impart beneficial properties to a catalyst system which are unexpected in view of what is known about the properties of bis(cyclopentadienyl) titanium compounds which are cocatalyzed by alumoxanes. Whereas titanocenes in their soluble form are generally unstable in the presence of aluminum alkyls, the monocyclopentadienyl titanium metal components of this invention, particularly those wherein the heteroatom is nitrogen, generally exhibit greater stability in the presence of aluminum alkyls, higher catalyst activity rates and higher α-olefin comonomer incorporation.

Further, the titanium species of the Group IV B transition metal component catalyst of this invention generally exhibit higher catalyst activities and the production of polymers of greater molecular weight and α-olefin comonomer contents than catalyst systems prepared with the zirconium or hafnium species of the Group IV B transition metal component.

A typical polymerization process of the invention such as for the polymerization or copolymerization of olefins comprises the steps of contacting ethylene or $C_3$–$C_{20}$ α-olefins alone, or with other unsaturated monomers including $C_3$–$C_{20}$ α-olefins, $C_4$–$C_{20}$ diolefins, and/or acetylenically unsaturated monomers either alone or in combination with other olefins and/or other unsaturated monomers, with a catalyst comprising, in a suitable polymerization diluent, the Group IV B transition metal component illustrated above; and a methylalumoxane in an amount to provide a molar aluminum to transition metal ratio of from about 1:1 to about 20,000:1 or more; and reacting such monomer in the presence of such catalyst system at a temperature of from about −100° C. to about 300° C. for a time of from about 1 second to about 10 hours to produce a polyolefin having a weight average molecular weight of from about 1,000 or less to about 5,000,000 or more and a molecular weight distribution of from about 1.5 to about 15.0.

DESCRIPTION OF THE PREFERRED EMBODIMENT

Catalyst Component

The Group IV B transition metal component of the catalyst system is represented by the general formula:

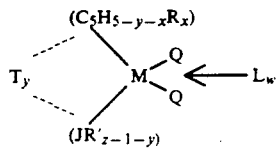

wherein
M is Zr, Hf or Ti in its highest formal oxidation state (+4, $d^0$ complex);

$(C_5H_{5-y-x}R_x)$ is a cyclopentadienyl ring which is substituted with from zero to five substituent groups R, "x" is 0, 2, 3, 4 or 5 denoting the degree of substitution, and each substituent group R is, independently, a radical selected from a group consisting of $C_1-C_{20}$ hydrocarbyl radicals, substituted $C_1-C_{20}$ hydrocarbyl radicals wherein one or more hydrogen atoms is replaced by a halogen radical, an amido radical, a phosphido radical, an alkoxy radical or any other radical containing a Lewis acidic or basic functionality, $C_1-C_{20}$ hydrocarbyl-substituted metalloid radicals wherein the metalloid is selected from the Group IV A of the Periodic Table of Elements; and halogen radicals, amido radicals, phosphido radicals, alkoxy radicals, alkylborido radicals or any other radical containing Lewis acidic or basic functionality; or $(C_5H_{5-y-x}R_x)$ is a cyclopentadienyl ring in which two adjacent R-groups are joined forming $C_4-C_{20}$ ring to give a saturated or unsaturated polycyclic cyclopentadienyl ligand such as indenyl, tetrahydroindenyl, fluorenyl or octahydrofluorenyl;

$(JR'_{z-1-y})$ is a heteroatom ligand in which J is an element with a coordination number of three from Group V A or an element with a coordination number of two from Group VI A of the Periodic Table of Elements, preferably nitrogen, phosphorus, oxygen or sulfur with nitrogen being preferred, and each R' is, independently, a radical selected from a group consisting of $C_1-C_{20}$ hydrocarbyl radicals, substituted $C_1-C_{20}$ hydrocarbyl radicals wherein one or more hydrogen atoms is replaced by a halogen radical, an amido radical, a phosphido radical, and alkoxy radical or any other radical containing a Lewis acidic or basic functionality, and "z" is the coordination number of the element J;

each Q is, independently, any univalent anionic ligand such as a halide, hydride, or substituted or unsubstituted $C_1-C_{20}$ hydrocarbyl, alkoxide, aryloxide, amide, arylamide, phosphide or arylphosphide, provided that where any Q is a hydrocarbyl such Q is different from $(C_5H_{5-y-x}R_x)$, or both Q together may be an alkylidene or a cyclometallated hydrocarbyl or any other divalent anionic chelating ligand;

"y" is 0 or 1 when w is greater than 0, and y is 1 when w equals 0; when "y" is 1, T is a covalent bridging group containing a Group IV A or V A element such as, but not limited to, a dialkyl, alkylaryl or diaryl silicon or germanium radical, alkyl or aryl phosphine or amine radical, or a hydrocarbyl radical such as methylene, ethylene and the like; and L is a neutral Lewis base such as diethylether, tetraethylammonium chloride tetrahydrofuran, dimethylaniline, aniline, trimethylphosphine, n-butylamine, and the like; and "w" is a number from 0 to 3; L can also be a second transition metal compound of the same type such that the two metal centers M and M' are bridged by Q and Q', wherein M' has the same meaning as M and Q' has the same meaning as Q. Such compounds are represented by the formula:

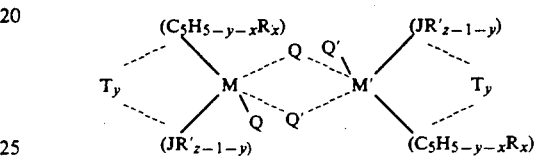

Examples of the T group which are suitable as a constituent group of the Group IV B transition metal component of the catalyst system are identified in column 1 of Table 1 under the heading "T".

Exemplary hydrocarbyl radicals for Q are methyl, ethyl, propyl, butyl, amyl, isoamyl, hexyl, isobutyl, heptyl, octyl, nonyl, decyl, cetyl, 2-ethylhexyl, phenyl and the like, with methyl being preferred. Exemplary halogen atoms for Q include chlorine, bromine, fluorine and iodine, with chlorine being preferred. Exemplary alkoxides and aryloxides for Q are methoxide, phenoxide and substituted phenoxides such as 4-methylphenoxide. Exemplary amides of Q are dimethylamide, diethylamide, methylethylamide, di-t-butylamide, diisoproylamide and the like. Exemplary aryl amides are diphenylamide and any other substituted phenyl amides. Exemplary phosphides of Q are diphenylphosphide, dicyclohexylphosphide, diethylphosphide, dimethylphosphide and the like. Exemplary alkyldiene radicals for both Q together are methylidene, ethylidene and propylidene. Examples of the Q group which are suitable as a constituent group or element of the Group IV B transition metal component of the catalyst system are identified in column 4 of Table 1 under the heading "Q".

Suitable hydrocarbyl and substituted hydrocarbyl radicals, which may be substituted as an R group for at least one hydrogen atom in the cyclopentadienyl ring, will contain from 1 to about 20 carbon atoms and include straight and branched alkyl radicals, cyclic hydrocarbon radicals, alkyl-substituted cyclic hydrocarbon radicals, aromatic radicals and alkyl-substituted aromatic radicals, amido-substituted hydrocarbon radicals, phosphido-substituted hydrocarbon radicals, alkoxy-substituted hydrocarbon radicals, alkylborido substituted radicals and cyclopentadienyl rings containing one or more fused saturated or unsaturated rings. Suitable organometallic radicals, which may be substituted as an R group for at least one hydrogen atom in the cyclopentadienyl ring, include trimethylsilyl, triethylsilyl, ethyldimethylsilyl, methyldiethylsilyl, triphenylgermyl, trimethylgermyl and the like. Other suitable radicals that may be substituted for one or more hydrogen atom in the cyclopentadienyl ring include halogen radicals, amido radicals, phosphido radicals, alkoxy radicals, alkylborido radicals and the like. Examples of cyclopentadienyl ring groups ($C_5H_{5-y-x}R_x$) which are suitable as a constituent group of the Group IV B transition metal component of the catalyst system are identified in Column 2 of Table 1 under the heading ($C_5H_{5-y-x}R_x$).

Suitable hydrocarbyl and substituted hydrocarbyl radicals, which may be used as an R' group in the heteroatom J ligand group, will contain from 1 to about 20 carbon atoms and include straight and branched alkyl radicals, cyclic hydrocarbon radicals, alkyl-substituted cyclic hydrocarbon radicals, aromatic radicals, alkyl-substituted aromatic radicals, halogen radicals, amido radicals, phosphido radicals alkylborido radicals, and the like. Examples of heteroatom ligand groups ($JR'_{z-1-y}$) which are suitable as a constituent group of the Group IV B transition metal component of the catalyst system are identified in column 3 of Table 1 under the heading ($JR'_{z-1-y}$).

Table 1 depicts representative constituent moieties for the "Group IV B transition metal component", the list is for illustrative purposes only and should not be construed to be limiting in any way. A number of final components may be formed by permuting all possible combinations of the constituent moieties with each other. Illustrative compounds are: dimethylsilyltetramethylcyclopentadienyl-tert-butylamido zirconium dichloride, dimethylsilyltetramethylcyclopentadienyl-tert-butylamido hafnium dichloride, dimethylsilyl-tert-butylcyclopentadienyl-tert-butylamido zirconium dichloride, dimethylsilyl-tert-butylcyclopentadienyl-tert-butylamido hafnium dichloride, dimethylsilyltrimethylsilylcyclopentadienyl-tert-butylamido zirconium dichloride, dimethylsilyltetramethylcyclopentadienyl-phenylamido zirconium dichloride, dimethylsilyltetramethylcyclopentadienylphenylamido hafnium dichloride, methylphenylsilyltetramethylcyclopentadienyl-tert-butylamido zirconium dichloride, methylphenylsilyltetramethylcyclopentadienyl-tert-butylamido hafnium dichloride, methylphenylsilyltetramethylcyclopentadienyl-tert-butylamido hafnium dimethyl, dimethylsilyltetramethylcyclopentadienyl-p-n-butylphenylamido zirconium dichloride, dimethylsilyltetramethylcyclopentadienyl-p-n-butylphenylamido hafnium dichloride.

As noted, titanium species of the Group IV B transition metal compound have generally been found to yield catalyst systems which in comparison to their zirconium or hafnium analogus, are of higher activity and α-olefin comonomer incorporating ability. Illustrative, but not limiting of the titanium species which exhibit such superior properties are methylphenylsilyltetramethylcyclopentadienyl-tert-butylamido titanium dichloride, dimethylsilyltetramethylcyclopentadienyl-p-n-butylphenylamido titanium dichloride, dimethylsilyltetramethylcyclopentadienyl-p-methoxyphenylamido titanium dichloride, dimethylsilyltert-butylcyclopentadienyl-2,5-di-tert-butylphenylamido titanium dichloride, dimethylsilylindenyl-tert-butylamido titanium dichloride, dimethylsilyltetramethylcyclopentadienylcyclohexylamido titanium dichloride, dimethylsilylfluorenylcyclohexylamido titanium dichloride, dimethylsilyltetramethylcyclopentadienylphenylamido titanium dichloride, dmethylsilyltetramethylcyclopentadienyl-tert-butylamido titanium dichloride, dimethylsilyltetramethylcyclopentadienylcyclododecylamido titanium dichloride, and the like.

For illustrative purposes, the above compounds and those permuted from Table 1 do not include the neutral Lewis base ligand (L). The conditions under which complexes containing neutral Lewis base ligands such as ether or those which form dimeric compounds is determined by the steric bulk of the ligands about the metal center. For example, the t-butyl group in $Me_2Si(Me_4C_5)(N-t-Bu)ZrCl_2$ has greater steric requirements than the phenyl group in $Me_2Si(Me_4C_5)(NPh)ZrCl_2 \cdot Et_2O$ thereby not permitting ether coordination in the former compound. Similarly, due to the decreased steric bulk of the trimethylsilylcyclopentadienyl group in $[Me_2Si(Me_3SiC_5H_3)(N-t-Bu)ZrCl_2]_2$ versus that of the tetramethylcyclopentadienyl group in $Me_2Si(Me_4C_5)(N-t-Bu)ZrCl_2$, the former compound is dimeric and the latter is not.

TABLE 1

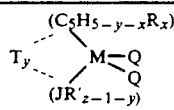

| T (when y = 1) | ($C_5H_{5-y-x}R_x$) | ($JR'_{z-1-y}$) | Q | M |
|---|---|---|---|---|
| dimethylsilyl | cyclopentadienyl | t-butylamide | hydride | zirconium |
| diethylsilyl | methylcyclopentadienyl | phenylamido | chloro | hafnium |
| di-n-propylsilyl | 1,2-dimethylcyclopentadienyl | p-n-butylphenylamido | methyl | titanium |
| diisopropylsilyl | 1,3-dimethylcyclopentadienyl | cyclohexylamido | ethyl | |
| di-n-butylsilyl | indenyl | perflurophenylamido | phenyl | |
| di-t-butylsilyl | 1,2-diethylcyclopentadienyl | n-butylamido | fluoro | |
| di-n-hexylsilyl | tetramethylcyclopentadienyl | methylamido | bromo | |
| methylphenylsilyl | ethylcyclopentadienyl | ethylamido | iodo | |
| ethylmethylsilyl | n-butylcyclopentadienyl | n-propylamido | n-propyl | |
| diphenylsilyl | cyclohexylmethylcyclopentadienyl | isopropylamido | isopropyl | |
| di(p-t-butylphenethylsilyl) | n-octylcyclopentadienyl | benzylamido | n-butyl | |
| n-hexylmethylsilyl | β-phenylpropylcyclopentadienyl | t-butylphosphido | amyl | |
| cyclopentamethylenesilyl | tetrahydroindenyl | ethylphosphido | isoamyl | |
| cyclotetramethylenesilyl | propylcyclopentadienyl | phenylphosphido | hexyl | |
| cyclotrimethylenesilyl | t-butylcyclopentadienyl | cyclohexylphosphido | isobutyl | |
| dimethylgermanyl | benzylcyclopentadienyl | oxo (when y = 1) | heptyl | |
| diethylgermanyl | diphenylmethylcyclopentadienyl | sulfido (when y = 1) | octyl | |
| phenylamido | trimethylgermylcyclopentadienyl | methoxide (when y = 0) | nonyl | |
| t-butylamido | trimethylstannnylcyclopentadienyl | ethoxide (when y = 0) | decyl | |
| methylamido | triethylplumbylcyclopentadienyl | methylthio (when y = 0) | cetyl | |
| t-butylphosphido | trifluromethylcyclopentadienyl | ethylthio (when y = 0) | methoxy | |

TABLE 1-continued $$T_y \overset{(C_5H_{5-y-x}R_x)}{\underset{(JR'_{z-1-y})}{\diagdown}} M \overset{Q}{\underset{Q}{\diagup}}$$

| T (when y = 1) | (C₅H₅₋ᵧ₋ₓRₓ) | (JR'ᵤ₋₁₋ᵧ) | Q | M |
| --- | --- | --- | --- | --- |
| ethylphosphido | trimethylsilylcyclopentadienyl | | ethoxy | |
| phenylphosphido | pentamethylcyclcopentadienyl (when y = 0) | | propoxy | |
| methylene | fluorenyl | | butoxy | |
| dimethylmethylene | octahydrofluorenyl | | phenoxy | |
| diethylmethylene | N,N-dimethylamidocyclopentadienyl | | dimethylamido | |
| ethylene | dimethylphosphidocyclopentadienyl | | diethylamido | |
| dimethylethylene | methoxycyclopentadienyl | | methylethylamido | |
| diethylethylene | dimethylboridocyclopentadienyl | | di-t-butylamido | |
| dipropylethylene | (N,N-dimethylamidomethyl)-cyclopentadienyl | | diphenylamido | |
| propylene | | | diphenylphosphido | |
| dimethylpropylene | | | dicyclohexylphosphido | |
| diethylpropylene | | | dimethylphosphido | |
| 1,1-dimethyl-3,3-dimethylpropylene | | | methylidene (both Q) | |
| tetramethyldisiloxane | | | ethylidene (both Q) | |
| 1,1,4,4-tetramethyldisilylethylene | | | propylidene (both Q) | |
| | | | ethyleneglycoldianion (both Q) | |

Generally the bridged species of the Group IV B transition metal compound ("y"=1) are preferred. These compounds can be prepared by reacting a cyclopentadienyl lithium compound with a dihalo compound whereupon a lithium halide salt is liberated and a monohalo substituent becomes covalently bound to the cyclopentadienyl compound. The so substituted cyclopentadienyl reaction product is next reacted with a lithium salt of a phosphide, oxide, sulfide or amide (for the sake of illustrative purposes, a lithium amide) whereupon the halo element of the monohalo substituent group of the reaction product reacts to liberate a lithium halide salt and the amine moiety of the lithium amide salt becomes covalently bound to the substituent of the cyclopentadienyl reaction product. The resulting amine derivative of the cyclopentadienyl product is then reacted with an alkyl lithium reagent whereupon the labile hydrogen atoms, at the carbon atom of the cyclopentadienyl compound and at the nitrogen atom of the amine moiety covalently bound to the substituent group, react with the alkyl of the lithium alkyl reagent to liberate the alkane and produce a dilithium salt of the cyclopentadienyl compound. Thereafter the bridged species of the Group IV B transition metal compound is produced by reacting the dilithium salt cyclopentadienyl compound with a Group IV B transition metal preferably a Group IV B transition metal halide.

Unbridged species of the Group IV B transition metal compound can be prepared from the reaction of a cyclopentadienyl lithium compound and a lithium salt of an amine with a Group IV B transition metal halide.

Suitable, but not limiting, Group IV B transition metal compounds which may be utilized in the catalyst system of this invention include those bridged species ("y"=1) wherein the T group bridge is a dialkyl, diaryl or alkylaryl silane, or methylene or ethylene. Exemplary of the more preferred species of bridged Group IV B transition metal compounds are dimethylsilyl, methylphenylsilyl, diethylsilyl, ethylphenylsilyl, diphenylsilyl, ethylene or methylene bridged compounds. Most preferred of the bridged species are dimethylsilyl, diethylsilyl and methylphenylsilyl bridged compounds.

Suitable Group IV B transition metal compounds which are illustrative of the unbridged ("y"=0) species which may be utilized in the catalyst systems of this invention are exemplified by pentamethylcyclopentadienyldi-t-butylphosphinodimethyl hafnium; pentamethylcyclopentadienyldi-t-butylphosphinomethylethyl hafnium; cyclopentadienyl-2-methylbutoxide dimethyl titanium.

To illustrate members of the Group IV B transition metal component, select any combination of the species in Table An example of a bridged species would be dimethylsilylcyclopentadienyl-t-butylamidodichloro zirconium; an example of an unbridged species would be cyclopentadienyldi-t-butylamidodichloro zirconium.

Generally, wherein it is desired to produce an α-olefin copolymer which incorporates a high content of α-olefin, while maintaining high polymer molecular weight the species of Group IV B transition metal compound preferred is one of titanium. The most preferred species of titanium metal compounds are represented by the formula:

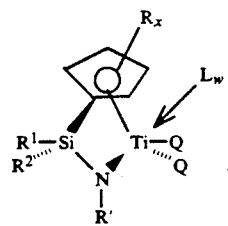

wherein Q, L, R', R, "x" and "w" are as previously defined and R¹ and R₂ are each independently a C₁ to C₂₀ hydrocarbyl radicals, substituted C₁ to C₂₀ hydrocarbyl radicals wherein one or more hydrogen atom is replaced by a halogen atom; R¹ and R² may also be joined forming a C₃ to C₂₀ ring which incorporates the silicon bridge.

The alumoxane component of the catalyst system is an oligomeric compound which may be represented by the general formula (R³-Al-O)ₘ which is a cyclic compound, or may be $R^4(R^5\text{-Al-O})_m\text{-AlR}^6{}_2$ which is a linear compound. An alumoxane is generally a mixture of both the linear and cyclic compounds. In the general alumoxane formula $R^3$, $R^4$, $R^5$ and $R^6$ are, independently a $C_1$-$C_5$ alkyl radical, for example, methyl, ethyl, propyl, butyl or pentyl and "m" is an integer from 1 to about 50. Most preferably, $R^3$, $R^4$, $R^5$ and $R^6$ are each methyl and "m" is at least 4. When an alkyl aluminum halide is employed in the preparation of the alumoxane, one or more $R^{3-6}$ groups may be halide.

As is now well known, alumoxanes can be prepared by various procedures. For example, a trialkyl aluminum may be reacted with water, in the form of a moist inert organic solvent; or the trialkyl aluminum may be contacted with a hydrated salt, such as hydrated copper sulfate suspended in an inert organic solvent, to yield an alumoxane. Generally, however prepared, the reaction of a trialkyl aluminum with a limited amount of water yields a mixture of both linear and cyclic species of alumoxane.

Suitable alumoxanes which may be utilized in the catalyst systems of this invention are those prepared by the hydrolysis of a trialkylaluminum; such as trimethylaluminum, triethyaluminum, tripropylaluminum; triisobutylaluminum, dimethylaluminumchloride, diisobutylaluminumchloride, diethylaluminumchloride, and the like. The most preferred alumoxane for use is methylalumoxane (MAO). Methylalumoxanes having an average degree of oligomerization of from about 4 to about 25 ("m"=4 to 25), with a range of 13 to 25, are the most preferred.

Catalyst Systems

The catalyst systems employed in the method of the invention comprise a complex formed upon admixture of the Group IV B transition metal component with an alumoxane component. The catalyst system may be prepared by addition of the requisite Group IV B transition metal and alumoxane components to an inert solvent in which olefin polymerization can be carried out by a solution, slurry or bulk phase or high pressure-high temperature polymerization procedure.

The catalyst system may be conveniently prepared by placing the selected Group IV B transition metal component and the selected alumoxane component, in any order of addition, in an alkane or aromatic hydrocarbon solvent—preferably one which is also suitable for service as a polymerization diluent. Where the hydrocarbon solvent utilized is also suitable for use as a polymerization diluent, the catalyst system may be prepared in situ in the polymerization reactor. Alternatively, the catalyst system may be separately prepared, in concentrated form, and added to the polymerization diluent in a reactor. Or, if desired, the components of the catalyst system may be prepared as separate solutions and added to the polymerization diluent in a reactor, in appropriate ratios, as is suitable for a continuous liquid phase polymerization reaction procedure. Alkane and aromatic hydrocarbons suitable as solvents for formation of the catalyst system and also as a polymerization diluent are exemplified by, but are not necessarily limited to, straight and branched chain hydrocarbons such as isobutane, butane, pentane, hexane, heptane, octane and the like, cyclic and alicyclic hydrocarbons such as cyclohexane, cycloheptane, methylcyclohexane, methylcycloheptane and the like, and aromatic and alkyl-substituted aromatic compounds such as benzene, toluene, xylene and the like. Suitable solvents also include liquid olefins which may act as monomers or comonomers including ethylene, propylene, 1-butene, 1-hexene and the like.

In accordance with this invention optimum results are generally obtained wherein the Group IV B transition metal compound is present in the polymerization diluent in a concentration of from about 0.0001 to about 1.0 millimoles/liter of diluent and the alumoxane component is present in an amount to provide a molar aluminum to transition metal ratio of from about 1:1 to about 20,000:1. Sufficient solvent should be employed so as to provide adequate heat transfer away from the catalyst components during reaction and to permit good mixing.

The catalyst system ingredients—that is, the Group IV B transition metal, the alumoxane, and polymerization diluent—can be added to the reaction vessel rapidly or slowly. The temperature maintained during the contact of the catalyst components can vary widely, such as, for example, from −100° to 300° C. Greater or lesser temperatures can also be employed. Preferably, during formation of the catalyst system, the reaction is maintained within a temperature of from about 25° to 100° C, most preferably about 25° C.

At all times, the individual catalyst system components, as well as the catalyst system once formed, are protected from oxygen and moisture. Therefore, the reactions to prepare the catalyst system are performed in an oxygen and moisture free atmosphere and, where the catalyst system is recovered separately it is recovered in an oxygen and moisture free atmosphere. Preferably, therefore, the reactions are performed in the presence of an inert dry gas such as, for example, helium or nitrogen.

Polymerization Process

In a preferred embodiment of the process of this invention the catalyst system is utilized in the liquid phase (slurry, solution, suspension or bulk phase or combination thereof), high pressure fluid phase or gas phase polymerization of an olefin monomer. These processes may be employed singularly or in series. The liquid phase process comprises the steps of contacting an olefin monomer with the catalyst system in a suitable polymerization diluent and reacting said monomer in the presence of said catalyst system for a time and at a temperature sufficient to produce a polyolefin of high molecular weight.

The monomer for such process may comprise ethylene alone, for the production of a homopolyethylene, or ethylene in combination with an o-olefin having 3 to 20 carbon atoms for the production of an ethylene-α-olefin copolymer. Homopolymers of higher α-olefin such as propylene, butene, styrene and copolymers thereof with ethylene and/or $C_4$ or higher α-olefins and diolefins can also be prepared. Conditions most preferred for the homo- or copolymerization of ethylene are those wherein ethylene is submitted to the reaction zone at pressures of from about 0.019 psia to about 50,000 psia and the reaction temperature is maintained at from about −100° to about 300° C. The aluminum to transition, metal molar ratio is preferably from about 1:1 to 20,000 to 1. A more preferable range would be 1:1 to 2000:1. The reaction time is preferably from about 10 seconds to about 10 hour. Without limiting in any way the scope of the invention, one means for carrying out the process of the present invention for production of a copolymer is as follows: in a stirred-tank reactor liquid α-olefin monomer is introduced, such as 1-butene. The catalyst system is introduced via nozzles in either the vapor or liquid phase. Feed ethylene gas is introduced either into the vapor phase of the reactor, or sparged into the liquid phase as is well known in the art. The reactor contains a liquid phase composed substantially of liquid α-olefin comonomer, together with dissolved ethylene gas, and a vapor phase containing vapors of all monomers. The reactor temperature and pressure may be controlled via reflux of vaporizing α-olefin monomer (autorefrigeration), as well as by cooling coils, jackets etc. The polymerization rate is controlled by the concentration of catalyst. The ethylene content of the polymer product is determined by the ratio of ethylene to α-olefin comonomer in the reactor, which is controlled by manipulating the relative feed rates of these components to the reactor.

As before noted, a catalyst system wherein the Group IV B transition metal component is a titanium species has the ability to incorporate high contents of α-olefin comonomers while maintaining high polymer molecular weights. Accordingly, the selection of the Group IV B transition metal component is another parameter which may be utilized as a control over the ethylene content of a copolymer within a reasonable ratio of ethylene to α-olefin comonomer.

EXAMPLES

In the examples which illustrate the practice of the invention the analytical techniques described below were employed for the analysis of the resulting polyolefin products. Molecular weight determinations for polyolefin products were made by Gel Permeation Chromatography (GPC) according to the following technique. Molecular weights and molecular weight distributions were measured using a waters 150 gel permeation chromatograph equipped with a differential refractive index (DRI) detector and a Chromatix KMX-6 on-line light scattering photometer. The system was used at 135° C. with 1,2,4-trichlorobenzene as the mobile phase. Shodex (Showa Denko America, Inc.) polystyrene gel columns 802, 803, 804 and 805 were used. This technique is discussed in "Liquid Chromatography of Polymers and Related Materials III", J. Cazes editor, Marcel Dekker. 1981, p. 207, which is incorporated herein by reference. No corrections for column spreading were employed; however, data on generally accepted standards, e.g. National Bureau of Standards Polyethylene 1484 and anionically produced hydrogenated polyisoprenes (an alternating ethylene-propylene copolymer) demonstrated that such corrections on Mw/Mn (=MWD) were less than 0.05 units. Mw/Mn was calculated from elution times. The numerical analyses were performed using the commercially available Beckman/CIS customized LALLS software in conjunction with the standard Gel Permeation package, run on a HP 1000 computer.

The following examples are intended to illustrate specific embodiments of the invention and are not intended to limit the scope of the invention.

All procedures were performed under an inert atmosphere of helium or nitrogen. Solvent choices are often optional, for example, in most cases either pentane or 30-60 petroleum ether can be interchanged. The lithiated amides were prepared from the corresponding amines and either D-BuLi or MeLi. Published methods for preparing LiHC$_5$Me$_4$ include C. M. Fendrick et al. *Organometallic*, 3, 819 (1984) and F. H. Khöler and K. H. Doll, Z. Naturforsch, 376, 144 (1982). Other lithiated substituted cyclopentadienyl compounds are typically prepared from the corresponding cyclopentadienyl ligand and n-BuLi or MeLi, or by reaction of MeLi with the proper fulvene. TiCl$_4$, ZrCl$_4$ and HfCl$_4$ were purchased from either Aldrich Chemical Company or Cerac. TiCl$_4$ was typically used in its etherate form. The etherate, TiCl$_4$·2Et$_2$O, can be prepared by gingerly adding TiCl$_4$ to diethylether. Amines, silanes and lithium reagents were Systems. Methylalumoxane was supplied by either Scherring or Ethyl Corp.

Examples A-L and AT-IT of Group IV B Transition Metal-Components

Example A

Compound A: Part 1. Me$_4$HC$_5$Li (10.0 g, 0.078 mol) was slowly added to a Me$_2$SiCl$_2$ (11.5 ml, 0.095 mol, in 225 ml of tetrahydrofuran (THF) solution). The solution was stirred for 1 hour to assure complete reaction. The thf solvent was then removed via a vacuum to a cold trap held at −196° C. Pentane was added to precipitate the LiCl. The mixture was filtered through Celite. The solvent was removed from the filtrate. Me$_4$HC$_5$SiMe$_2$Cl (15.34 g. 0.071 mol) was recovered as a pale yellow liquid.

Part 2. Me$_4$HC$_5$SiMe$_2$Cl (10.0 g, 0.047 mol) was slowly added to a suspension of LiHN-t-Bu (3.68 g, 0.047 mol, ~100 ml of THF). The mixture was stirred overnight. The THF was then removed via a vacuum to a cold trap held at −196° C. Petroleum ether (~100 ml) was added to precipitate the LiCl. The mixture was filtered through Celite. The solvent was removed from the filtrate Me$_2$Si(Me$_4$HC$_5$)(HN-st-Bu) (11.14 g. 0.044 mol) was isolated as a pale yellow liquid.

Part 3. Me$_2$Si(Me$_4$HC$_5$)(HN-t-Bu) (11.14 g, 0.044 mol was diluted with ~100 ml of Et$_2$O. MeLi (1.4 M, 64 ml, 0.090 mol) was slowly added. The mixture was allowed to stir for ½ hour after the final addition of MeLi. The ether was reduced in volume prior to filtering off the product. The product, [Me$_2$Si(Me$_4$C$_5$)(N-t-Bu)]Li$_2$, was washed with several small portions of ether, then vacuum dried.

Part 4. [Me$_2$Si(Me$_4$C$_5$)(N-t-Bu)]Li$_2$ (3.0 g, 0.011 mol) was suspended in ~150 ml of Et$_2$O. ZrCl$_4$ (2.65 g, 0.011 mol) was slowly added and the resulting mixture was allowed to stir overnight. The ether was removed via a vacuum to a cold trap held at −196° C. Pentane was added to precipitate the LiCl. The mixture was filtered through Celite twice. The pentane was significantly reduced in volume and the pale yellow solid was filtered off and washed with solvent. Me$_2$Si(Me$_4$C$_5$)(N-t-Bu)ZrCl$_2$ (1.07 g, 0.0026 mole) was recovered. Additional Me$_2$Si(Me$_4$C$_5$)(N-t-Bu)ZrCl$_2$ was recovered from the filtrate by repeating the recrystallization procedure. Total yield, 1.94 g, 0.0047 mol.

EXAMPLE B

Compound B: The same procedure of Example A for preparing compound A was followed with the exception of the use of HfCl$_4$ in place of ZrCl$_4$ in Part 4. Thus, when [Me$_2$Si(Me$_4$C$_5$)(N-t-Bu)]Li$_2$ (2.13 g, 0.0081 mol) and HfCl$_4$ (2.59 g, 0.0081 mol) were used, Me$_2$Si(Me$_4$C$_5$)(N-t-Bu)HfCl$_2$ 0.98 g, 0.0020 mol) was produced.

EXAMPLE C

Compound C: Part 1. Me$_2$SiCl$_2$ (7.5 ml, 0.062 mol) was diluted with ~30 ml of THF. A t-BuH$_4$C$_5$Li solution (7.29 g, 0.056 mol, ~100 ml THF) was slowly added, and the resulting mixture was allowed to stir overnight. The thf was removed via a vacuum to a trap held at −196° C. Pentane was added to precipitate the LiCl, and the mixture was filtered through Celite. The pentane was removed from the filtrate leaving behind a pale yellow liquid, t-BuH$_4$C$_5$SiMe$_2$Cl (10.4 g, 0.048 mol).

Part 2. To a THF solution of LiHN-t-Bu (3.83 g, 0.048 mol, ~125 ml), t-BuH$_4$C$_5$SiMe$_2$Cl (10.4 g, 0.048 mol) was added drop wise. The resulting solution was allowed to stir overnight. The THF, was removed via a vacuum to a trap held at −196° C. Pentane was added to precipitate the LiCl, and the mixture was filtered through Celite. The pentane was removed from the filtrate leaving behind a pale yellow liquid, Me$_2$Si(t-BuH$_4$C$_5$)(NH-t-Bu) (11.4 g, 0.045 mol).

Part 3. Me$_2$Si(t-BuH$_4$C$_5$)(NH-t-Bu) (11.4 g, 0.045 mol) was diluted with ~100 ml Et$_2$O. MeLi (1.4M, 70 ml, 0.098 mol) was slowly added. The mixture was allowed to stir overnight. The ether was removed via a vacuum to a trap held at −196° C., leaving behind a pale yellow solid, [Me$_2$Si(t-BuH$_3$C$_5$)(N-t-Bu)]Li$_2$ (11.9 g, 0.045 mol).

Part 4. [Me$_2$Si(t-BuH$_3$C$_5$)(N-t-Bu)]Li$_2$ (3.39 g 0.013 mol) was suspended in ~100 ml of Et$_2$O. ZrCl$_4$ (3.0 g, 0.013 mol) was slowly added. The mixture was allowed to stir overnight. The ether was removed and pentane was added to precipitate the LiCl. The mixture was filtered through Celite. The pentane solution was reduced in volume, and the pale tan solid was filtered off and washed several times with small quantities of pentane. The product of empirical formula Me$_2$Si(t-BuH$_3$C$_5$)(N-t-Bu)ZrCl$_2$ (2.43 g, 0.0059 mol) was isolated.

EXAMPLE D

Compound D: The same procedure of Example C for preparing compound C was followed with the exception of the use of HfCl$_4$ in Part 4. Thus, when [Me$_2$Si(t-BuH$_3$C$_5$)(N-t-Bu)]Li$_2$ (3.29 g, 0.012 mol) and HfCl$_4$(4.0 g, 0.012 mol) were used, the product of the empirical formula [Me$_2$Si(t-BuH$_3$C$_5$)(N-t-Bu)HfCl$_2$ (1.86 g, 0.0037 mol) was produced.

EXAMPLE E

Compound E: Part 1. Me$_2$SiCl$_2$ (7.0 g. 0.054 mol) was diluted with ~100 ml of ether. Me$_3$SiC$_5$H$_4$Li (5.9 g, 0.041 mol) was slowly added. Approximately 75 ml of thf was added and the mixture was allowed to stir overnight. The solvent was removed via a vacuum to a cold trap held at −196° C. Pentane was added to precipitate the LiCl. The mixture was filtered through Celite. The solvent was removed from the filtrate giving Me$_2$Si(Me$_3$SiC$_5$H$_4$)Cl (8.1 g, 0.035 mol) as a pale yellow liquid.

Part 2. Me$_2$Si(Me$_3$SiC$_5$H$_4$)Cl (3.96 g. 0.017 mol) was diluted with ~50 ml of ether. LiHN-t-Bu (1.36 g, 0.017 mol) was slowly added, and the mixture was allowed to stir overnight. The ether was removed via a vacuum and pentane was added to precipitate the LiCl. The mixture was filtered through Celite, and the pentane was removed from the filtrate. Me$_2$Si(Me$_3$SiC$_5$H$_4$)(NH-t-Bu) (3.7 g, 0.014 mol) was isolated as a pale yellow liquid.

Part 3. Me$_2$Si(M$_3$SiC$_5$H$_4$)(NH-t-Bu) (3.7 g, 0.014 mol) as diluted with ether. MeLi (25 ml, 1.4 M in ether, 0.035 mol) was slowly added. The mixture was allowed to stir for 1.5 hours after the final addition of MeLi. The ether was removed via vacuum producing 4.6 g of a white solid formulated as Li$_2$[Me$_2$Si(Me$_3$SiC$_5$H$_3$)(N-t-Bu)]·⅔Et$_2$O and unreacted MeLi which was not removed from the solid.

Part 4. Li$_2$[Me$_2$Si(Me$_3$SiC$_5$H$_3$)(N-t-Bu)]·⅔Et$_2$O (1.44 g, 0.0043 mol) was suspended in ~50 ml of ether. ZrCl$_4$ (1.0 g, 0.0043 mol) was slowly added and the reaction was allowed to stir for a few hours. The solvent was removed via vacuum and pentane was added to precipitate the LiCl. The mixture was filtered through Celite, and the filtrate was reduced in volume. The flask was placed in the freezer (−40° C.) to maximize precipitation of the product. The solid was filtered off giving 0.273 g of an off-white solid. The filtrate was again reduced in volume, the precipitate filtered off to give an additional 0.345 g for a total of 0.62 g of the compound with emperical formula Me$_2$Si(Me$_3$SiC$_5$H$_3$) (N-t-Bu)ZrCl$_2$. The x-ray crystal structure of this product reveals that the compound is dimeric in nature.

EXAMPLE F

Compound F: Part 1. Me$_4$HC$_5$SiMe$_2$Cl was prepared as described in Example A for the preparation of compound A, Part 1.

Part 2. LiHNPh (4.6 g, 0.0462 mol) was dissolved in ~100 ml of THF. Me$_4$HC$_5$SiMe$_2$Cl (10.0 g. 0.0466 mol) was slowly added. The mixture was allowed to stir overnight. The THF was removed via a vacuum. Petroleum ether and toluene were added to precipitate the LiCl, and the mixture was filtered through Celite. The solvent was removed, leaving behind a dark yellow liquid, Me$_2$Si(Me$_4$HC$_5$)(NHPh) (10.5 g, 0.0387 mol).

Part 3. Me$_2$Si(Me$_4$HC$_5$)(NHPh) (10.5g, 0.0387 mol) was diluted with ~60 ml of ether. MeLi (1.4M in ether, 56 ml, 0.0784 mol) was slowly added and the reaction was allowed to stir overnight. The resulting white solid, (11.0 g), was filtered off Li$_2$[Me$_2$Si(Me$_4$C$_5$)(NPh)]·⅔Et$_2$O and was washed with ether.

Part 4. Li$_2$[Me$_2$Si(Me$_4$C$_5$) (NPh)]·⅔Et$_2$O (2.81 g, 0.083 mol) was suspended in ~40 ml of ether. ZrCl$_4$ (1.92 g. 0.0082 mol) was slowly added and the mixture as allowed to stir overnight. The ether was removed via a vacuum, and a mixture of petroleum ether and toluene was added to precipitate the LiCl. The mixture was filtered through Celite, the solvent mixture was removed via vacuum, and pentane was added. The mixture was placed in the freezer at −40° C. to maximize the precipitation of the product. The solid was then filtered off and washed with pentane. Me$_2$Si(Me$_4$C$_5$)(NPh)ZrCl$_2$·Et$_2$O was recovered as a pale yellow solid (1.89 g).

EXAMPLE G

Compound G: The same procedure of Example F for preparing compound F was followed with the exception of the use of HfCl$_4$ in place of ZrCl$_4$ in Part 4. Thus, when Li$_2$[Me$_2$Si(Me$_4$C$_5$)(NPh)]·⅔Et$_2$O (2.0 g, 0.0059 mol) and HfCl$_4$ (1.89 g, 0.0059 mol) were used, Me$_2$Si(Me$_4$C$_5$)(NPh)HfCl$_2$ ·⅔Et$_2$O (1.70 g) was produced.

EXAMPLE H

Compound H: Part 1. MePhSiCl$_2$ (14.9 g, 0.078 mol) was diluted with ~250 ml of THF. Me$_4$C$_5$HLi (10.0 g. 0.078 mol) was slowly added as a solid. The reaction solution was allowed to stir overnight. The solvent was removed via a vacuum to a cold trap held at −196° C. Petroleum ether was added to precipitate the LiCl. The mixture was filtered through Celite, and the pentane was removed from the filtrate. MePhSi(Me$_4$C$_5$H)Cl (20.8 g, 0.075 mol) was isolated as a yellow viscous liquid.

Part 2. LiHN-t-Bu (4.28 g, 0.054 mol) was dissolved in ~100 ml of THF. MePhSi(Me$_4$C$_5$H)Cl (15.0 g, 0.054 mol) was added drop wise. The yellow solution was allowed to stir overnight. The solvent was removed via vacuum. Petroleum ether was added to precipitate the LiCl. The mixture was filtered through Celite, and the filtrate was evaporated down. MePhSi(Me$_4$C$_5$H)(NH-t-Bu) (16.6 g, 0.053 mol) was recovered as an extremely viscous liquid.

Part 3. MePhSi(Me$_4$C$_5$H)(NH-t-Bu) (16.6 g, 0.053 mol) was diluted with ~100 ml of ether. MeLi (76 ml, 0.106 mol, 1.4 M) was slowly added and the reaction mixture was allowed to stir for ~3 hours. The ether was reduced in volume and the lithium salt was filtered off and washed with pentane producing 20.0 g of a pale yellow solid formulated as Li$_2$[MePhSi(Me$_4$C$_5$)(N-t-Bu)]·⅜Et$_2$O.

Part 4. Li$_2$[MePhSi(Me$_4$C$_5$)(N-t-Bu)]·⅜Et$_2$O (5.0 g, 0.0131 mol) was suspended in ~100 ml of Et$_2$O. ZrCl$_4$ (3.06 g, 0.0131 mol) was slowly added. The reaction mixture was allowed to stir at room temperature for ~1.5 hours over which time the reaction mixture slightly darkened in color. The solvent was removed via vacuum and a mixture of petroleum ether and toluene was added. The mixture was filtered through Celite to remove the LiCl. The filtrate was evaporated down to near dryness and filtered off. The off white solid was washed with petroleum ether. The yield of product, MePhSi(Me$_4$C$_5$)(N-t-Bu)ZrCl$_2$, was 3.82 g (0.0081 mol).

EXAMPLE I

Compound I: Li$_2$[MePhSi(Me$_4$C$_5$)(N-t-Bu)]·⅜Et$_2$O was prepared as described in Example H for the preparation of compound H, Part 3.

Part 4. Li$_2$[MePhSi(Me$_4$C$_5$)(N-t-Bu)]·⅜Et$_2$O (5.00 g, 0.0131 mol) was suspended in ~100 ml of Et$_2$O. HfCl$_4$ (4.20 g, 0.0131 mol) was slowly added and the reaction mixture was allowed to stir overnight. The solvent was removed via vacuum and petroleum ether was added to precipitate the LiCl. The mixture was filtered through Celite. The filtrate was evaporated down to near dryness and filtered off. The off-white solid was washed with petroleum ether. MePhSi(Me$_4$C$_5$)(N-t-Bu)HfCl$_2$ was recovered (3.54 g, 0.0058 mole).

EXAMPLE J

Compound J: MePhSi(Me$_4$C$_5$)(N-t-Bu)HfMe$_2$ was prepared by adding a stoichiometric amount of MeLi (1.4M in ether) to MePhSi(Me$_4$C$_5$)(N-t-Bu)HfCl2 suspended in ether. The white solid was isolated in near quantitative yield.

EXAMPLE K

Compound K: Part Me$_4$C$_5$SiMe$_2$Cl was prepared as described in Example A for the preparation of compound A, Part 1.

Part 2. Me$_4$C$_5$SiMe$_2$Cl (10.0 g, 0.047 mol) was diluted with ~25 ml of Et$_2$O. LiHNC$_5$H$_4$-p-n-Bu·1/10Et$_2$O (7.57 g, 0.047 mol) was added slowly. The mixture was allowed to stir for −3 hours. The solvent was removed via vacuum. Petroleum ether was added to precipitate the LiCl, and the mixture was filtered through Celite. The solvent was removed leaving behind an orange viscous liquid, Me$_2$Si(Me$_4$C$_5$H)(HNCl$_6$H$_4$-p-t-Bu) (12.7 g, 0.039 mol).

Part 3. Me$_2$Si(Me$_4$C$_5$H)(HNC$_6$H$_4$-p-n-Bu) (12.7 g. 0.039 mol) was dilute with ~50 ml of Et$_2$O. MeLi (1.4M, 55 ml, 0.077 mol) was slowly added. The mixture was allowed to stir for ~3 hours. The product was filtered off and washed with Et$_2$O producing Li$_2$[Me$_2$Si(Me$_4$C$_5$)(NC$_6$H$_4$-p-n-Bu)]·⅜Et$_2$O as a white solid (13.1 g, 0.033 mol).

Part 4. Li$_2$[Me$_2$Si(Me$_4$C$_5$)(NC$_6$H$_4$-p-n-Bu)]·⅜Et$_2$O 3.45 g, 0.0087 mol) was suspended in ~50 ml of Et$_2$O. ZrCl$_4$ (2.0 g, 0.0086 mol) was slowly added and the mixture was allowed to stir overnight. The ether was removed via vacuum, and petroleum ether was added to precipitate the LiCl. The mixture was filtered through Celite. The filtrate was evaporated to dryness to give a yellow solid which was recrystallized from pentane and identified as Me$_2$Si(Me$_4$C$_5$)(NC$_6$H$_4$-p-n-Bu)ZrCl$_2$·⅜Et$_2$O (4.2 g).

EXAMPLE L

Compound L: Li$_2$[MeSi(Me$_4$C$_5$)(NC$_6$H$_4$-p-n-Bu].3/4Et2O was prepared as described in Example K for the preparation of compound K, Part 3.

Part 4. Li$_2$[Me$_2$Si(Me$_4$C$_5$)(NC$_6$H$_4$-p-n-Bu)·⅜Et$_2$O (3.77 g., 0.0095 mol) was suspended in ~50 ml of Et$_2$O. HfCl$_4$ (3.0 g, 0.0094 mol) was slowly added as a solid and the mixture was allowed to stir overnight. The ether was removed via vacuum and petroleum ether was added to precipitate out the LiCl. The mixture was filtered through Celite. Petroleum ether was removed via a vacuum giving an off-white solid which was recrystallized from pentane. The product was identified as Me$_2$Si(Me$_4$C$_5$)(NC$_6$H$_4$-p-n-Bu)HfCl$_2$ (1.54 g, 0.0027 mol).

EXAMPLE AT

Compound AT: Part 1. MePhSiCl$_2$ (14.9 g, 0.078 mol) was diluted with 250 ml of THF. Me$_4$HC$_5$Li (10.0 g, 0.078 mol) was slowly added as a solid. The reaction solution was allowed to stir overnight. The solvent was removed via a vacuum to a cold trap held at −196° C. Petroleum ether was added to precipitate the LiCl. The mixture was filtered through Celite and the pentane was removed from the filtrate. MePhSi(Me$_4$C$_5$H)Cl (20.8 g, 0.075 mol) was isolated as a yellow viscous liquid.

Part 2. LiHN-t-Bu (4.28 g, 0.054 mol) was dissolved in ~100 ml of THF. MePhSi(C$_5$Me$_4$H)Cl (15.0 g, 0.054 mol) was added dropwise. The yellow solution was allowed to stir overnight. The solvent was removed in vacuo. Petroleum ether was added to precipitate the LiCl. The mixture was filtered through Celite, and the filtrate was evaporated. MePhSi(C$_5$Me$_4$H)(NH-t-Bu) (16.6 g, 0.053 mol) was recovered as an extremely viscous liquid.

Part 3. MePhSi(C$_5$Me$_4$H)(NH-t-Bu)(17.2 g, 0.055 mol) was diluted with ~20 ml of ether. n-BuLi (60 ml in hexane, 0.096 mol, 1.6M) was slowly added and the reaction mixture was allowed to stir for ~3 hours. The solvent was removed in vacuo to yield 15.5 g (0.48 mol) of a pale tan solid formulated as Li$_2$[MePhSi(C$_5$Me$_4$)(N-t-Bu)].

Part 4. Li$_2$[MePhSi(C$_5$Me$_4$)(N-t-Bu)](8.75 g, 0.027 mol) was suspended in ~125 ml of cold ether (~ −30° C.). TiCl$_4$·2Et$_2$O(9.1 g, 0.027 mol) was slowly added. The reaction was allowed to stir for several hours prior to removing the ether via vacuum. A mixture of toluene and dichloromethane was then added to solubilize the product. The mixture was filtered through Celite to remove the LiCl. The solvent was largely removed via vacuum and petroleum ether was added. The mixture was cooled to maximize product precipitation. The crude product was filtered off and redissolved in toluene. The toluene insolubles were filtered off. The toluene was then reduced in volume and petroleum ether was added. The mixture was cooled to maximize precipitation prior to filtering off 3.34 g (7.76 mmol) of the yellow solid MePhSi($C_5Me_4$)(N-t-Bu)$TiCl_2$.

EXAMPLE BT

Compound BT: Part 1. $C_5Me_4HLi$ (10.0 g, 0.078 mol) was slowly added to a $Me_2SiCl_2$ solution (11.5 ml, 0.095 mol, in 225 ml of tetrahydrofuran). The solution was stirred for 1 hour to assure a complete reaction. The solvent was then removed in vacuo. Pentane was added to precipitate the LiCl. The mixture was filtered through Celite and the solvent was removed from the filtrate in vacuo. ($C_5Me_4H$)$SiMe_2Cl$ (15.34 g, 0.071 mol) was recovered as a pale yellow liquid.

Part 2. ($C_5Me_4H$)$SiMe_2Cl$ (10.0 g, 0.047 mol) was diluted with ~25 ml of $Et_2O$. $LiHNC_6H_4$-p-n-Bu·1/10$Et_2O$ (7.75 g, 0.048 mol) was added slowly. The mixture was allowed to stir for ~3 hours. The solvent was removed in vacuo. Petroleum ether was added to precipitate the LiCl, and the mixture was filtered through Celite. The solvent was removed leaving behind an orange viscous liquid, $Me_2Si(C_5Me_4H)(HNC_6H_4$-p-n-Bu)(12.7 g, 0.039 mol).

Part 3. $Me_2Si(C_5Me_4H)(HNC_6H_4$-p-n-Bu)(12.7 g, 0.039 mol) was diluted with ~50 ml of $Et_2O$. MeLi (1.4M, 55 ml, 0.077 mol) was slowly added. The mixture was allowed to stir for ~3 hours. The product was filtered off and washed with $Et_2O$ and dried. $Li_2[Me_2Si(C_5Me_4)(NC_6H_4$-p-n-Bu)]·⅔$Et_2O$ was isolated as a white solid (13.1 g, 0.033 mol).

Part 4. $Li_2[Me_2Si(C_5Me_4)(NC_6H_4$-p-n-Bu)]·⅔$Et_2O$ (2.36 g, 5.97 mmol) was suspended in cold ether. $TiCl_4$·2$Et_2O$(2.0g, 5.92 mmol) was slowly added. The mixture was allowed to stir overnight. The solvent was removed via vacuum and petroleum ether and dichloromethane were added. The mixture was filtered through Celite to remove the LiCl. The solvent was removed via vacuum, and toluene and petroleum ether were added. After refrigeration, the mixture was filtered off, producing an off yellow product. This was redissolved in dichloromethane, followed by the addition of petroleum ether. The mixture was then refrigerated prior to filtering off 0.83 g (1.87 mmol) of the yellow solid, $Me_2Si(C_5Me_4)(NC_6H_4$-p-n-Bu)$TiCl_2O$.

EXAMPLE CT

Compound CT: Part 1. ($C_5Me_4H$)$SiMe_2Cl$ was prepared as described in Example BT for the preparation of compound BT, Part 1.

Part 2. ($C_5Me_4H$)$SiMe_2Cl$ (8.14 g, 0.038 mol) was mixed with ~100 ml of THF. $LiHNC_6H_4$-p-OMe (4.89 g, 0.038 mol) was slowly added and the mixture was allowed to stir for 2 hours. The solvent was removed via vacuum and petroleum ether was added to precipitate the LiCl which was filtered off. The solvent was removed from the filtrate via vacuum and the product $Me_2Si(C_5Me_4H)(NC_6H_4$-p-OMe) (9.8 g, 0.033 mol) was isolated as a viscous orange-yellow liquid.

Part 3 $Me_2Si(C_5Me_4H)(HNC_6H_4$-p-OMe)(10.0 g, 0.033 mol) was diluted with THF. MeLi (47 ml, 1.4M in ether, 0.066 mol) was slowly added and the mixture was allowed to stir for a few hours. The solvent was then removed in vacuo leaving behind a white solid coordinated by thf.

The product was formulated as $Li_2[Me_2Si(C_5Me_4)(NC_6H_4$-p-OMe)]·2THF (14.7 g, 0.032 mol).

Part 4. $Li_2[Me_2Si(C_5Me_4)(NC_6H_4$-p-OMe)]·2THF (7.0 g, 0.015 mol) was suspended in ~125 ml of cold ether. $TiCl_4$·2$Et_2O$ (5.1 g, 0.015 mol) was slowly added and the mixture was allowed to stir overnight. The solvent was removed via vacuum and petroleum ether, dichloromethane and toluene were added. The mixture was filtered through Celite to remove the LiCl. The solvent was reduced in volume and petroleum ether was added. The mixture was refrigerated, after which a brown solid was filtered off. Multiple extractions and recrystallizations from toluene and petroleum ether yielded 2.3 g (5.5 mmol) of $Me_2Si(C_5Me_4)(NC_6H_4$-p-OMe)$TiCl_2$.

EXAMPLE DT

Compound DT: Part 1. $Me_2SiCl_2$ (7.5 ml, 0.062 mol) was diluted with ~30 ml of THF. A t-$BuH_4C_5Li$ solution (7.29 g, 0.057 mol, ~100 ml of THF) was slowly added, and the resulting mixture was allowed to stir overnight. The THF was removed in vacuo. Pentane was added to precipitate the LiCl, and the mixture was filtered through Celite. The pentane was removed from the filtrate leaving behind a pale yellow liquid, (t-$BuC_5H_4$)$SiMe_2Cl$ (10.4 g, 0.048 mo)).

Part 2. (t-$BuC_5H_4$)$SiMe_2Cl$ (5.0 g, 0.023 mol) was added to ~50 ml of THF. $LiHN$-2,5-t-$Bu_2C_6H_3$ (4.94 g, 0.023 mol) was slowly added and the reaction mixture was allowed to stir for 2 hours. The solvent was removed via vacuum and petroleum ether was added to precipitate the LiCl which was filtered off. The solvent was removed from the filtrate yielding an oily/solid material, $Me_2Si(t$-$Bu_2C_5H_4)(HN$-2,5-t-$Bu_2C_6H_3$).

Part 3. To the above material, $Me_2Si(t$-$BuC_5H_4)(HN$-2,5-t-$Bu_2C_6H_3$) (assumed to be ~8 g, 0.021 mol), MeLi (30 ml, 1.4M in ether, 0.042 mol) was slowly added. The mixture was allowed to stir for a few hours prior to removing the solvent via vacuum. The slightly pinkish solid was washed with ether, filtered and dried yielding 4.42 g (0.011 mol) of $Li_2[Me_2Si(t$-$BuC_5H_3)(N$-2,5-t-$Bu_2C_6H_3$)].

Part 4. $Li_2[Me_2Si(t$-$BuC_5H_3)(N$-2,5-t-$Bu_2C_6H_3$)](7.6 g, 0.019 mol) was suspended in cold ether. $TiCl_4$·2$Et_2O$ (6.5 g, 0.019 mol) was slowly added and the mixture was allowed to stir overnight. The solvent was removed via vacuum and toluene and dichloromethane were added. The mixture was filtered through Celite to remove the LiCl. The filtrate was reduced in volume and petroleum ether was added. The mixture was chilled to maximize precipitation. A dark yellow solid was filtered off and was recrystallized from toluene and petroleum ether giving a tan solid. A total of 1.6 g (3.2 mmol) of $Me_2Si(t$-$BuC_5H_3)(N$-2,5-t-$Bu_2C_6H_3)TiCl_2$ was isolated.

EXAMPLE ET

Compound ET: Part 1. $LiC_9H_7$ (40 g, 0.33 mol, lithiated indene=Li(Hind)) was slowly added to $Me_2SiCl_2$ (60 ml, 0.49 mol) in ether and THF. The reaction was allowed to stir for 1.5 hours prior to removing the solvent via vacuum. Petroleum ether was then added, and the LiCl was filtered off. The solvent was removed from the filtrate via vacuum, leaving behind the pale yellow liquid, (Hind)$Me_2SiCl$(55.7 g, 0.27 mol).

Part 2. (Hind)Me$_2$SiCl(20.0 g, 0.096 mol) was diluted with ether. LiHN-t-Bu(7.6 g, 0.096 mol) was slowly added and the mixture was allowed to stir overnight. The solvent was removed via vacuum and petroleum ether and toluene were added. The LiCl was filtered off and the solvent was removed via vacuum to give the product, Me$_2$Si(Hind)(HN-t-Bu).

Part 3. Me$_2$Si(Hind)(HN-t-Bu)(21 g, 0.086 mol) was diluted with a mixture of petroleum ether and diethyl ether. t-BuLi (108 ml, 1.6M in hexanes, 0.17 mol) was slowly added and the mixture was allowed to stir overnight. The solvent was removed via vacuum and the remaining solid was washed with petroleum ether and filtered off. Li$_2$[Me$_2$Si(ind)(N-t-Bu)]·$\frac{1}{4}$Et$_2$O was isolated as a pale yellow solid (26 g, 0.094 mol).

Part 4. Li $_2$[Me$_2$Si(ind)(N-t-Bu)]·$\frac{1}{4}$Et$_2$O(10 g, 0.036 mol) was dissolved in ether. TiCl$_4$·2Et$_2$O(12.1 g, 0.036 mol) was added to the cold solution. The reaction was allowed to stir overnight prior to removal of the solvent via vacuum. A mixture of toluene and dichloromethane were added and the mixture was filtered through Celite to remove the LiCl. The solvent was removed and hot toluene was added. The insolubles were filtered off. The solution was reduced in volume and petroleum ether was added. The mixture was chilled prior to filtering off the solid, Me$_2$Si(ind)(N-t-Bu)TiCl$_2$, which was recrystallized several times. The final yield was 2.5 g (6.8 mmol).

EXAMPLE FT

Compound FT: Part 1. (C$_5$Me$_4$H)SiMe$_2$Cl was prepared as described in Example BT for the preparation of compound BT, Part 1.

Part 2. (C$_5$Me$_4$H)SiMe$_2$Cl (5.19 g, 0.024 mol) was slowly added to a solution of LiHNC$_6$H$_{11}$ (2.52 g, 0.024 mol) in ~125 ml of THF. The solution was allowed to stir for several hours. The THF was removed via vacuum and petroleum ether was added to precipitate the LiCl which was filtered off. The solvent was removed from the filtrate via vacuum yielding 6.3 g (0.023 mol) of the yellow liquid, Me$_2$Si(C$_5$Me$_4$H)(HNC$_6$H$_{11}$).

Part 3. Me$_2$Si(C$_5$Me$_4$H)(HNC$_6$H$_{11}$)(6.3 g, 0.023 mol) was diluted with ~100 ml of ether. MeLi (33 ml, 1.4M in ether, 0.046 mol) was slowly added and the mixture was allowed to stir for 0.5 hours prior to filtering off the white solid. The solid was washed with ether and vacuum dried. Li$_2$[Me$_2$Si(C$_5$Me$_4$)(NC$_6$H$_{11}$)] was isolated in a 5.4 g (0.019 mol) yield.

Part 4. Li$_2$[Me$_2$Si(C$_5$Me$_4$)(NC$_6$H$_{11}$)] (2.57 g, 8.90 mmol) was suspended in ~50 ml of cold ether. TiCl$_4$ 2Et$_2$O (3.0 g, 8.9 mmol) was slowly added and the mixture was allowed to stir overnight. The solvent was removed via vacuum and a mixture of toluene and dichloromethane was added. The mixture was filtered through Celite to remove the LiCl byproduct. The solvent was removed from the filtrate and a small portion of toluene was added followed by petroleum ether. The mixture was chilled in order to maximize precipitation. A brown solid was filtered off which was initially dissolved in hot toluene, filtered through Celite, and reduced in volume. Petroleum ether was then added. After refrigeration, an olive green solid was filtered off. This solid was recrystallized twice from dichloromethane and petroleum ether to give a final yield of 0.94 g (2.4 mmol) of the pale olive green solid, Me$_2$Si(C$_5$Me$_4$)(NC$_6$H$_{11}$)TiCl.

EXAMPLE GT

Compound GT: Part 1. Me$_2$SiCl$_2$ (150 ml, 1.24 mol) was diluted with ~200 ml of Et$_2$O. Li(C$_{13}$H$_9$)·Et$_2$O (lithiated fluorene etherate, 28.2 g, 0.11 mol) was slowly added. The reaction was allowed to stir for ~1 hour prior to removing the solvent via vacuum. Toluene was added and the mixture was filtered through Celite to remove the LiCl. The solvent was removed from the filtrate, leaving behind the off-white solid, Me$_2$Si(C$_{13}$H$_9$) Cl (25.4 g, 0.096 mol).

Part 2. Me$_2$Si(C$_{13}$H$_9$)Cl (8.0 g, 0.031 mol) was suspended in ether and THF in a ratio of 5:1. LiHNC$_6$H$_{11}$ (3.25 g, 0.031 mol) was slowly added. The reaction mixture was allowed to stir overnight. After removal of the solvent via vacuum, toluene was added and the mixture was filtered through Celite to remove the LiCl. The filtrate was reduced in volume to give a viscous orange liquid. To this liquid which was diluted in Et$_2$O, 43 ml of 1.4M MeLi (0.060 mol) was added slowly. The mixture was allowed to stir overnight. The solvent was removed in vacuo to produce 13.0 g (0.031 mol) of Li$_2$[Me$_2$Si(C$_{13}$H$_8$)(NC$_6$H$_{11}$)]·1.25 Et$_2$O.

Part 3. Li$_2$[Me$_2$Si(C$_{13}$H$_8$)(NC$_6$H$_{11}$)]·1.25 Et$_2$O (6.5 g, 0.015 mol) was dissolved in cold ether. TiCl$_4$ 2Et$_2$O (5.16 g, 0.015 mol) was slowly added. The mixture was allowed to stir overnight. The solvent was removed via vacuum and methylene chloride was added. The mixture was filtered through Celite to remove the LiCl. The filtrate was reduced in volume and petroleum ether was added. This was refrigerated to maximize precipitation prior to filtering off the solid. Since the solid collected was not completely soluble in toluene, it was mixed with toluene and filtered. The filtrate was reduced in volume and petroleum ether was added to induce precipitation. The mixture was refrigerated prior to filtration. The red-brown solid Me$_2$Si(C$_{13}$H$_8$)(NC$_6$H$_{11}$)TiCl$_2$ was isolated (2.3 g, 5.2 mol).

EXAMPLE HT

Compound HT: Part 1. (C$_5$Me$_4$H)SiMe$_2$Cl was prepared as described in Example BT for the preparation of compound BT, Part 1.

Part. 2 LiHNPh (4.6 g, 0.046 mol) was dissolved in ~100 ml of THF. (C$_5$Me$_4$H)SiMe$_2$Cl (10.0 g, 0.047 mol) was slowly added. The mixture was allowed to stir overnight. The THF was removed in vacuo. Petroleum ether and toluene were added to precipitate the LiCl, and the mixture was filtered through Celite. The solvent was removed, leaving behind a dark yellow liquid, Me$_2$Si(C$_5$Me$_4$H)(NHPh) (10.5 g, 0.039 mol).

Part 3. Me$_2$Si(C$_5$Me$_4$H)(NHPh) (9.33 g, 0.034 mol) was diluted with ~30 ml of ether. MeLi (1.4M in ether, 44 ml, 0.062 mol) was slowly added and the reaction was allowed to stir for 2 hours. After reducing the volume of the solvent, the resulting white solid, Li$_2$[Me$_2$Si(C$_5$Me$_4$)(NPh)]·$\frac{1}{2}$Et$_2$O (9.7 g, 0.030 mol), was filtered off washed with ether and dried.

Part 4. Li$_2$[Me$_2$Si(C$_5$Me$_4$(NPh)]·$\frac{1}{2}$Et$_2$O (4.3 g, 0.013 mol) was suspended in ~50 ml of cold ether. TiCl$_4$ 2Et$_2$O (4.10 g, 0.012 mol) was slowly added, and the mixture was allowed to stir for several hours. The solvent was removed in vacuo, and toluene and dichloromethane were added to solubilize the product. The mixture was filtered through Celite to remove the LiCl. The solvent was removed in vacuo and a small portion of toluene was added along with petroleum ether. The mixture was refrigerated in order to maximize precipitation of a tan solid which was filtered off. The solid was washed with a small portion of toluene and the remaining solid was redissolved in hot toluene and filtered through Celite to remove the toluene insolubles. The toluene was then removed to produce 2.32 g (5.98 mmol) of the yellow solid, $Me_2Si(C_5Me_4)(NPh)TiCl_2$

EXAMPLE IT

Compound IT: Part 1. $(C_5Me_4H)SiMe_2Cl$ was prepared as described in Example BT for the preparation of Compound BT, part 1.

Part 2. $(C_5Me_4H)SiMe_2Cl$ (10.0 g, 0.047 mol) was slowly added to a suspension of LiHN-t-Bu (3.68 g, 0.047 mol, ~100 ml thf). The mixture was stirred overnight. The thf was then removed via a vacuum to a cold trap held at $-196°$ C. Petroleum ether was added to precipitate the LiCl. The mixture was filtered through Celite. The solvent was removed from the filtrate. $Me_2Si(C_5Me_4H)(NH-t-Bu)$ (11.14 g, 0.044 mol) was isolated as a pale yellow liquid.

Part 3. $Me_2Si(C_5Me_4H)(NH-t-Bu)(11.14$ g, 0.044 mol) was diluted with ~100 ml of ether. MeLi (1.4M, 64 ml, 0.090 mol) was slowly added. The mixture was allowed to stir for $\frac{1}{2}$ hour after the final addition of MeLi. The ether was reduced in volume prior to filtering off the product. The product, $[Me_2Si(C_5Me_4)(N-t-Bu)]Li_2$, was washed with several small portions of ether, then vacuum dried.

Part 4. $[Me_2Si(C_5Me_4)(N-t-Bu)Li_2$ (6.6 g, 0.025 mol) was suspended in cold ether. $TiCl_4 \cdot 2Et_2O$(8.4 g, 0.025 mol) was slowly added and the resulting mixture was allowed to stir overnight. The ether was removed via a vacuum to a cold trap held at $-196°$ C. Methylene chloride was added to precipitate the LiCl. The mixture was filtered through Celite. The solvent was significantly reduced in volume and petroleum ether was added to precipitate the product. This mixture was refrigerated prior to filtration in order to maximize precipitation. $Me_2Si(C_5Me_4)(N-t-Bu)TiCl_2$ was isolated (2.1 g, 5.7 mmol).

EXAMPLE JT

Compound JT: Part 1. $(C_5Me_4H)SiMe_2Cl$ was prepared as described in Example BT for the preparation of Compound BT, Part 1.

Part 2. $(C_5Me_4H)SiMe_2Cl$ (8.0 g, 0.037 mol) was slowly added to a suspension of $LiHNC_{12}H_{23}$ ($C_{12}H_{23}$=cyclododecyl, 7.0 g, 0.037 mol, ~80 ml thf). The mixture was stirred overnight. The thf was then removed via a vacuum to a cold trap held at $-196°$ C. Petroleum ether and toluene was added to precipitate the LiCl. The mixture was filtered through Celite. The solvent was removed from the filtrate. $Me_2Si(C_5Me_4H)(NHC_{12}H_{23})$(11.8 g, 0.033 mol) was isolated as a pale yellow liquid.

Part 3. $Me_2Si(C_5Me_4H)(NHC_{12}H_{23})(11.9$ g, 0.033 mol) was diluted with ~150 ml of ether. MeLi (1.4M, 47 ml, 0.066 mol) was slowly added. The mixture was allowed to stir for 2 hours after the final addition of MeLi. The ether was reduced in volume prior to filtering off the product. The product, $[Me_2Si(C_5Me_4)(NC_{12}H_{23})]Li_2$, was washed with several small portions of ether, then vacuum dried to yield 11.1 g (0.030 mol) of product.

Part 4. $[Me_2Si(C_5Me_4)(NC_{12}H_{23})]Li_2$ (3.0 g, 0.008 mol) was suspended in cold ether. $TiCl_4$ $2Et_2O$ (2.7 g, 0.008 mol) was slowly added and the resulting mixture was allowed to stir overnight. The ether was removed via a vacuum to a cold trap held at $-196°$ C. Methylene chloride was added to precipitate the LiCl. The mixture was filtered through Celite. The solvent was significantly reduced in volume and petroleum ether was added to precipitate the product. This mixture was refrigerated prior to filtration in order to maxmize precipitation. The solid collected was recrystallized from methylene chloride and $Me_2Si(C_5Me_4)(NC_{12}H_{23})TiCl_2$ was isolated (1.0 g, 2.1 mmol).

Examples 1-70 of Polymerization

EXAMPLE 1

Polymerization—Compound A

The polymerization run was performed in a 1-liter autoclave reactor equipped with a paddle stirrer, an external water jacket for temperature control, a regulated supply of dry nitrogen, ethylene, propylene, 1-butene and hexane, and a septum inlet for introduction of other solvents, transition metal compound and alumoxane solutions. The reactor was dried and degassed thoroughly prior to use. A typical run consisted of injecting 400 ml of toluene, 6 ml of 1.5M MAO, and 0.23 mg of compound A (0.2 ml of a 11.5 mg in 10 ml of toluene solution) into the reactor. The reactor was then heated to 80° C. and the ethylene (60 psi) was introduced into the system. The solvent was evaporated off of the polymer by a stream of nitrogen. Polyethylene was recovered (9.2 g, MW=257,200 MWD=2.275).

EXAMPLE 2

Polymerization Compound A

The polymerization was carried out as in Example 1 with the following changes: 300 ml of toluene, 3 ml of 1.5M MAO, and 0.115 mg of compound A (0.1 ml of a 11.5 mg in 10 ml of toluene solutions). Polyethylene was recovered (3.8 g, MW=359,800, MWD=2.425).

EXAMPLE 3

Polymerization—Compound A

The polymerization was carried out as in Example 2 using the identical concentrations. The difference involved running the reaction at 40° C. rather than 80° C. as in the previous example. Polyethylene was recovered (2.4 g, MW=635,000, MWD=3.445).

EXAMPLE 4

Polymerization—Compound A

The polymerization was carried out as in Example 1 1 except for the use of 300 ml of hexane in place of 400 ml of toluene. Polyethylene was recovered (5.4 g, MW=212,600, MWD=2.849).

EXAMPLE 5

Polymerization—Compound A

Using the same reactor design and general procedure as in Example 1, 300 ml of toluene, 200 ml of propylene, 6.0 ml of 1.5 M MAO, and 0.46 mg of compound A (0.4 ml of a 11.5 mg in 10 ml of toluene solution) was introduced into the reactor. The reactor was heated to 80° C., the ethylene was added (60 psi), and the reaction was allowed to run for 30 minutes, followed by rapidly cooling and venting the system. After evaporation of the solvent, 13.3 g of an ethylene-propylene copolymer was recovered (MW=24,900, MWD=2.027, 73.5 SCB/1000C by IR).

EXAMPLE 6

Polymerization—Compound A

The polymerization was carried out as in Example 5 except with the following changes: 200 ml of toluene and 0.92 mg of compound A (0.8 ml of a 11.5 mg in 10 ml of toluene solution). The reaction temperature was also reduce to 50° C. An ethylene-propylene copolymer was recovered (6.0 g, MW=83,100, MWD=2.370, 75.7 SCB/1000C by IR).

EXAMPLE 7

Polymerization—Compound A

Using the same reactor design and general procedure as in Example 1, 150 ml of toluene, 100 ml of 1-butene, 6.0 ml of 1.5 M MAO, and 2.3 mg of compound A (2.0 ml of a 11.5 mg in 10 ml of toluene solution) were added to the reactor. The reactor was heated at 50° C., the ethylene was introduced (65 psi), and the reaction was allowed to run for 30 minutes, followed by rapidly cooling and venting the system. After evaporation of the toluene, 25.4 g of an ethylene-1-butene copolymer was recovered (MW=184,500, MWD=3.424, 23.5 SCB/1000C by $^{13}$C NMR and 21.5 SCB/1000C by IR).

EXAMPLE 8

Polymerization—Compound A

The polymerization was carried out as in Example 7 except with the following changes: 100 ml of toluene and 150 ml of 1-butene. An ethylene-1-butene copolyer was recovered (30.2 g, MW=143,500, MWD=3.097, 30.8 SCB/1000C by $^{13}$C NMR and 26.5 SCB/1000C by IR).

EXAMPLE 9

Polymerization—Compound A

The polymerization was carried out as in Example 7 except with the following changes: 200 ml of toluene, 8.0 ml of 1.0M MAO, and 50 ml of 1-butene. An ethylene-1-butene copolymer was recovered (24.9 g, MW=163,200, MWD=3.290, 23.3 SCB/1000C by $^{13}$C NMR and 18.9 SCB/1000C by IR).

EXAMPLE 10

Polymerization—Compound A

The polymerization was carried out as in Example 9 except for the replacement of 200 ml of toluene with 200 ml of hexane. An ethylene-1-butene copolymer was recovered (19.5 g, MW=150,600, MWD=3.510, 12.1 SCB/1000C by $^{13}$C NMR and 12.7 SCB/1000C by IR).

EXAMPLE 11

Polymerization—Compound A

The polymerization was carried out as in Example 10 except with the following changes: 150 ml of hexane, and 100 ml of 1-butene. An ethylene-1-butene copolymer was recovered (16.0 g, MW=116,200, MWD=3.158, 19.2 SCB/1000C by $^{13}$C NMR and 19.4 SCB/1000C by IR).

EXAMPLE 12

Polymerization—Compound A

Using the same reactor design and general procedure as described in Example 1, 400 ml of toluene, 5.0 ml of 1.0M MAO, and 0.2 ml of a preactivated compound A solution (11.5 mg of compound A dissolved in 9.0 ml of toluene and 1.0 ml of 1.0M MAO) were added to the reactor. The reactor was heated to 80° C., and ethylene was introduced (60 psi), and the reactor was allowed to run for 30 minutes, followed by rapidly cooling and venting the system. After evaporation of the solvent, 3.4 g of polyethylene was recovered (MW=285,000, MWD=2.808).

EXAMPLE 13

Polymerization—Compound A

A polymerization was carried out as in Example 12 with exception of aging the preactivated compound A solution by one day. Polyethylene was recovered (2.0 g, MW=260,700, MWD=2.738).

EXAMPLE 14

Polymerization—Compound A

Using the same reactor design and general procedure as described in Example 1, 400 ml of toluene, 0.25 ml of 1.0 M MAO, and 0.2 ml of a preactivated compound A solution (11.5 mg of compound A dissolved in 9.5 ml of toluene and 0.5 ml of 1.0M MAO) were added into the reactor. The reactor was heated to 80° C. and ethylene was introduced (60 psi), and the reactor was allowed to run for 30 minutes, followed by rapidly cooling and venting the system. After evaporation of the solvent, 1.1 g of polyethylene was recovered (MW=479,600, MWD=3.130).

EXAMPLE 15

Polymerization—Compound A

Using the same reactor design and general procedure as described in Example 1, 400 ml of toluene and 2.0 ml of a preactivated compound A solution (11.5 mg of compound A dissolved in 9.5 ml of toluene and 0.5 ml of 1.0M MAO) were added into the reactor. The reactor was heated to 80° C. and ethylene was introduced (60 psi), and the reaction was allowed to run for 30 minutes, followed by rapidly cooling and venting the system. After evaporation of the solvent, 1.6 g of polyethylene was recovered (MW=458,800, MWD=2.037).

EXAMPLE 16

Polymerization—Compound A

Using the general procedure as described in Example 1, 400 ml of toluene, 5.0 ml of 1.0M MAO, 0.23 mg of compound A (0.2 ml of a 11.5 mg in 10 ml of toluene solution) was added to the reactor. The reactor was heated to 80° C., the ethylene introduced (400 psi), and the reaction was allowed to run for 30 minutes, followed by rapidly cooling and venting the system. After evaporation of the solvent, 19.4 g of polyethylene was recovered (MW=343,700, MWD=3.674).

EXAMPLE 17

Polymerization—Compound A

The polymerization was performed in a stirred 100 ml stainless steel autoclave which was equipped to perform polymerizations at pressures up to 40,000 psi and temperatures up to 300° C. The reactor was purged with nitrogen and heated to 160° C. Compound A and alumoxane solutions were prepared in separate vials. A stock solution was prepared by dissolving 26 mg of compound A in 100 ml of toluene. The compound A solution was prepared by diluting 0.5 ml of the stock solution with 5.0 ml of toluene. The alumoxane solution consisted of 2.0 ml of a 4% MAO solution added to 5.0 ml of toluene. The compound A solution was added to the alumoxane solution, then 0.43 ml of the mixed solutions were transferred by nitrogen pressure into a constant-volume injection tube. The autoclave was pressurized with ethylene to 1784 bar and was stirred at 1500 rpm. The mixed solutions were injected into the stirred reactor with excess pressure, at which time a temperature rise of 4° C. was observed. The temperature and pressure were recorded continuously for 120 seconds, at which time the contents of the autoclave were rapidly vented into a receiving vessel. The reactor was washed with xylene to recover any additional polymer remaining. These washings were combined with the polymer released when the autoclave was vented to yield 0.7 g of polyethylene (MW=245,500, MWD=2.257).

EXAMPLE 18

Polymerization—Compound B

Using the general procedure described in Example 1, 400 ml of toluene, 5.0 ml of 1.0M MAO and 0.278 mg of compound B (0.2 ml of a 13.9 mg in 10 ml of toluene solution) were added to the reactor. The reactor was heated to 80° C. and the ethylene (60 psi) was introduced into the system. The polymerization reaction was limited to 10 minutes. The reaction was ceased by rapidly cooling and venting the system. The solvent was evaporated off the polymer by a stream of nitrogen. Polyethylene was recovered (9.6 g, MW=241,200, MWD=2.628).

EXAMPLE 19

Polymerization—Compound C

Using the general procedures described in Example 1, 300 ml of toluene, 4.0 ml of 1.0M MAO and 0.46 mg of compound C (0.4 ml of a 11.5 mg in 10 ml of toluene solution) was added to the reactor. The reactor was heated to 80° C. and the ethylene (60 psi) was introduced into the system. The polymerization reaction was limited to 30 minutes. The reaction was ceased by rapidly cooling and venting the system. The solvent was evaporated off the polymer by a stream of nitrogen. Polyethylene was recovered (1.7 g, MW=278,400, MWD=2.142).

EXAMPLE 20

Polymerization—Compound D

Using the general procedure described in Example 1, 400 ml of toluene, 5.0 ml of 1.0 M MAO and 0.278 m of compound D (0.2 ml of a 13.9 mg in 10 ml of toluene solution) was added to the reactor. The reactor was heated to 80° C. and ethylene (60 psi) was introduced into the system. The polymerization reaction was limited to 30 minutes. The reaction was ceased by rapidly cooling and venting the system. The solvent was evaporated off the polymer by a stream of nitrogen. Polyethylene was recovered (1.9 g, MW=229,700, MWD=2.618).

EXAMPLE 21

Polymerization—Compound E

Using the general procedure described in Example 1, 1,300 ml of hexane, 9.0 ml of 1.0M MAO and 0.24 mg of compound E (0.2 ml of a 12.0 mg in 10 ml of toluene solution) was added to the reactor. The reactor was heated to 80° C. and ethylene (60 psi) was introduced into the system. The polymerization reaction was limited to 30 minutes. The reaction was ceased by rapidly cooling and venting the system. The solvent was evaporated off the polymer by a stream of nitrogen. Polyethylene was recovered (2.2 g, MW=258,200, MWD=2.348).

EXAMPLE 22

Polymerization Compound E

The polymerization was carried out as in Example 1 except with the following reactor conditions: 200 ml of toluene, 100 ml of 1-butene, 9.0 ml of 1.0M MAO and 2.4 mg of compound E (2.0 ml of a 12.0 mg in 10 ml of toluene solution) at 50° C. The reactor was pressurized with ethylene (65 psi), and the reaction was allowed to run for 30 minutes, followed by rapidly cooling and venting the system. After evaporation of the solvent, 1.8 g of an ethylene-1-butene copolymer was recovered (MW=323,600, MWD=2.463, 33.5 SCB/1000C by IR).

EXAMPLE 23

Polymerization—Compound F

The polymerization was carried out as in Example 1 with the following reactor conditions: 400 ml of toluene, 5.0 ml of 1.0M MAO, 0.242 mg of compound F (0.2 ml of a 12.1 mg in 10 ml of toluene solution), 80° C., 60 psi ethylene, 30 minutes. The run provided 5.3 g of polyethylene (MW=319,900, MWD=2.477).

EXAMPLE 24

Polymerization—Compound F

The polymerization was carried out as in Example 1 with the following reactor conditions: 150 ml of toluene, 100 ml of 1-butene, 9.0 ml of 1.0M MAO, 2.42 mg of compound F (2.0 ml of a 12.1 mg in 10 ml of toluene solution), 50° C., 65 psi ethylene, 30 minutes. The run provided 3.5 g of an ethylene-1-butene copolymer (MW=251,300, MWD=3.341, 33.3 SCB/1000C by IR).

EXAMPLE 25

Polymerization—Compound G

The polymerization was carried out as in Example 1 with the following reactor conditions: 400 ml of toluene, 5.0 ml of 1.0M MAO, 0.29 mg of compound G (0.2 ml of a 14.5 mg in 10 ml of toluene solution), 80° C., 60 psi ethylene, 30 minutes. The run provided 3.5 g of polyethylene (MW=237,300, MWD=2.549).

EXAMPLE 26

Polymerization—Compound G

The polymerization was carried out as in Example 1 with the following reactor conditions: 150 ml of toluene, 100 ml of 1-butene, 7.0 ml of 1.0M MAO, 2.9 mg of compound G (2.0 ml of a 14.5 mg in 10 ml of toluene solution), 50° C., 65 psi ethylene, 30 minutes. The run provided 7.0 g of an ethylene-1-butene copolymer (MW=425,000, MWD=2.816, 27.1 SCB/1000C by IR).

EXAMPLE 27

Polymerization—Compound H

The polymerization was carried out as in Example 1 with the following reactor conditions: 400 ml of toluene, 5.0 ml of 1.0M MAO, 0.266 mg of compound H (0.2 ml of a 13.3 mg in 10 ml of toluene solution), 80° C., 60 psi ethylene, 30 minutes. The run provided 11.1 g of polyethylene (MW=299,800, MWD=2.569).

EXAMPLE 28

Polymerization—Compound H

The polymerization was carried out as in Example 1 with the following reactor conditions: 150 ml of toluene, 100 ml of 1-butene, 7.0 ml of 1.0M MAO, 2.66 mg of compound H (2.0 ml of a 13.3 mg in 10 ml of toluene solution), 50° C., 65 psi ethylene, 30 minutes. The run provided 15.4 g of an ethylene-1-butene copolymer (MW=286,600, MWD=2.980, 45.4 SCB/1000C by IR).

EXAMPLE 29

Polymerization—Compound I

The polymerization was carried out as in Example 1 with the following reactor conditions: 400 ml of toluene, 5.0 ml of 1.0MAO, and 0.34 mg of compound I (0.2 ml of a 17.0 mg in 10 ml of toluene solution). The reactor was heated to 80° C., the ethylene was introduced (60 psi), and the reaction was allowed to run for 30 minutes, followed by rapidly cooling and venting the system. After evaporation of the solvent, 0.9 g of polyethylene was recovered (MW=377,000, MWD=1.996).

EXAMPLE 30

Polymerization—Compound J

The polymerization was carried out as in Example 1 with the following reactor conditions: 400 ml of toluene, 5.0 ml of 1.0M MAO, 0.318 mg of compound J (0.2 ml of a 15.9 mg in 10 ml of toluene solutions), 80° C., 60 psi ethylene, 30 minutes. The run provided 8.6 g of polyethylene (MW=321,000, MWD=2.803).

EXAMPLE 31

Polymerization—Compound J

The polymerization was carried out as in Example 1 with the following reactor conditions: 150 ml of toluene, 100 ml of 1-butene, 7.0 ml of 1.0M MAO, 3.18 mg of compound J (2.0 ml of a 15.9 mg in 10 ml of toluene solution), 50° C., 65 psi ethylene, 30 minutes. The run provided 11.2 g of an ethylene-1 -butene copolymer (MW=224,800, MWD=2.512, 49.6 SCB/1000C by IR technique, 55.4 SCB/1000C by NMR).

EXAMPLE 32

Polymerization—Compound K

The polymerization was carried out as in Example 1 with the following reactor conditions: 300 ml of toluene, 5.0 ml of 1.0M MAO, 0.272 mg of compound K (0.2 ml of a 13.6 mg in 10 ml of toluene solution), 80° C., 60 psi ethylene, 30 minutes. The run provided 26.6 g of polyethylene (MW=187,300, MWD=2.401).

EXAMPLE 33

Polymerization—Compound K

The polymerization was carried out as in Example 1 with the following reactor conditions: 150 ml of toluene, 100 ml of 1-butene, 7.0 ml of 1.0M MAO, 2.72 mg of compound K (2.0 ml of a 13.6 mg in 10 ml of toluene solution), 50° C., 65 psi ethylene, 30 minutes. The run provided 3.9 g of an ethylene-1-butene copolymer (MW=207,600, MWD=2.394, 33.9 SCB/1000C by IR).

EXAMPLE 34

Polymerization—Compound L

The polymerization was carried out as in Example 1 with the following reactor conditions: 400 ml of toluene, 5.0 ml of 1.0M MAO, 0.322 mg of compound L (0.2 ml of a 16.1 mg in 10 ml of toluene solution), 80° C., 60 psi ethylene, 30 minutes. The run provided 5.5 g of polyethylene (MW=174,300, MWD=2.193).

EXAMPLE 35

Polymerization—Compound A

The polymerization was carried out as in Example 1 with the following reactor contents: 250 ml of toluene, 150 ml of 1-hexene, 7.0 ml of 1.0M MAO and 2.3 mg of compound A (2.0 ml of a 11.5 mg in 10 ml of toluene solution) at 50° C. The reactor was pressurized with ethylene (65 psi), and the reaction was allowed to run for 30 minutes, followed by rapidly cooling and venting the system. After evaporation of the solvent, 26.5 g of an ethylene-1-hexane copolymer was recovered (MW=222,800, MWD=3.373, 39.1 SCB/1000C by IR).

EXAMPLE 36

Polymerization—Compound A

The polymerization was carried out as in Example 1 with the following reactor contents: 300 ml of toluene, 100 ml of 1-octene, 7.0 ml of 1.0M MAO and 2.3 mg of compound A (2.0 ml of a 11 5 mg in 10 ml of toluene solution) at 50° C. The reactor was pressurized with ethylene (65 psi), and the reaction was allowed to run for 30 minutes, followed by rapidly cooling and venting the system. After evaporation of the solvent, 19.7 g of an ethylene-1-octene copolymer was recovered (MW=48,600, MWD=3.007, 16.5 SCB/1000C by $^{13}$C NMR).

EXAMPLE 37

Polymerization—Compound A

The polymerization was carried out as in Example 1 with the following reactor conditions: 300 ml of toluene, 100 ml of 4-methyl-1-pentene, 7.0 ml of 1.0M MAO and 2.3 mg of compound A (2.0 ml of a 11.5 mg in 10 ml of toluene solution) at 50° C. The reactor was pressurized with ethyleme (65 psi), and the reaction was allowed to run for 30 minutes, followed by rapidly cooling and venting the system. After evaporation of the solvent, 15.1 g of an ethylene-4-methyl-1-pentene copolymer was recovered (MW=611,800, MWD=1.683, 1.8 mole % determined by $^{13}$C NMR).

EXAMPLE 38

Polymerization—Compound A

The polymerization was carried out as in Example 1 with the following reactor conditions: 300 ml of toluene, 100 ml of a 2.2M norbornene in toluene solution, 7.0 ml of 1.0M MAO and 2.3 mg of compound A (2.0 ml of a 11.5 mg in 10 ml of toluene solution) at 50° C. The reactor was pressurized with ethylene (65 psi), and the reaction was allowed to run for 30 minutes, followed by rapidly cooling and venting the system. After evaporation of the solvent, 12.3 g of an ethylene-norbornene copolymer was recovered (Mw=812,600, MWD=1.711, 0.3 mole % determined by $^{13}$C NMR).

EXAMPLE 39

Polymerization—Compound A

The polymerization was carried out as in Example 1 with the following reactor contents: 300 ml of toluene, 100 ml of cis-1,4-hexadiene, 7.0 ml of 1.0M MAO and 2.3 mg of compound A (2.0 ml of a 11.5 mg in 10 ml of toluene solution) at 50° C. The reactor was pressurized with ethylene (65 psi), and the reaction was allowed to run for 30 minutes, followed by rapidly cooling and venting the system. After evaporation of the solvent, 13.6 g of an ethylene-cis-1,4-hexadiene copolymer was recovered (MW=163,400, MWD=2.388, 2.2 mole % determined $^{13}$C NMR).

EXAMPLE 40

Polymerization—Compound AT

The polymerization run was performed in a 12 liter autoclave reactor equipped with a paddle stirrer, an external water jacket for temperature control, a regulated supply of dry nitrogen, ethylene, propylene, 1-butene and hexane, and a septum inlet for introduction of other solvents or comonomers, transition metal compound and alumoxane solutions. The reactor was dried and degassed thoroughly prior to use. A typical run consisted of injecting 400 ml of toluene, 5 ml of 1.0M MAO, 0.206 mg compound AT (0.2 ml of a 10.3 mg in 10 ml of toluene solution) into the reactor. The reactor was then heated to 80° C. and the ethylene (60 psi) was introduced into the system. The polymerization reaction was limited to 30 minutes. The reaction was ceased by rapidly cooling and venting the system. The solvent was evaporated off of the polymer by a stream of nitrogen. Polyethylene was recovered (11.8 g, MW=279,700, MWD=2.676).

EXAMPLE 41

Polymerization—Compound AT

Using the same reactor design and general procedure as described in Example 40, 400 ml of toluene, 5.0 ml of 1.0M MAO, and 0.2 ml of a preactivated compound AT solution (10.3 mg of compound AT dissolved in 9.5 ml of toluene and 0.5 ml of 1.0M MAO) were added to the reactor. The reactor was heated to 80° C., the ethylene was introduced (60 psi), and the reaction was allowed to run for 30 minutes, followed by rapidly cooling and venting the system. After evaporation of the solvent, 14.5 g of polyethylene was recovered (MW=406,100, MWD =2.486).

EXAMPLE 42

Polymerization—Compound AT

Using the same reactor design and general procedure described in Example 40. 300 ml of toluene, 100 ml of 1-hexene, 7.0 ml of 1.0M MAO, and 1.03 mg of compound AT (1.0 ml of 10.3 mg in 10 ml of toluene solution) were added to the reactor. The reactor was heated at 80° C., the ethylene was introduced (65 psi), and the reaction was allowed to run for 10 minutes, followed by rapidly cooling and venting the system. After evaporation of the toluene, 48.6 g of an ethylene-1-hexene copolymer was recovered (MW=98,500, MWD=1.745, 117 SCB/1000C by $^{13}$C NMR).

EXAMPLE 43

Polymerization—Compound AT

Using the same reactor design and general procedure described in Example 40, 375 ml of toluene, 25 ml of 1-hexene, 7.0 ml of 1.0M MAO, and 1.03 mg of compound AT (1.0 ml of a 10.3 mg in 10 ml of toluene solution) were added to the reactor. The reactor was heated at 80° C., the ethylene was introduced (65 psi), and the reaction was allowed to run for 10 minutes, followed by rapidly cooling and venting the system. After evaporation of the toluene, 29.2 g of an ethylene-1-hexene copolymer was recovered (MW=129,800, MWD=2.557, 53.0 SCB/1000C by $^{13}$C NMR).

EXAMPLE 44

Polymerization—Compound AT

Using the same reactor design and general procedure described in Example 40, 375 ml of toluene, 25 ml of 1-hexene, 7.0 ml of 1.0M MAO, and 1.03 mg of compound AT (1.0 ml of 10.3 mg in 10 ml of toluene solution) were added to the reactor. The reactor was heated at 50° C., the ethylene was introduced (65 psi), and the reaction was allowed to run for 10 minutes, followed by rapidly cooling and venting the system. After evaporation of the toluene, 15.0 g of an ethylene-1-hexene copolymer was recovered (MW=310,000, MWD=2.579, 47.2 SCB/1000C by $^{13}$C NMR).

EXAMPLE 45

Polymerization—Compound AT

Using the same reactor design and general procedure described in Example 40, 300 ml of toluene, 100ml of propylene, 7.0 ml of 1.0M MAO, and 2.06 mg of compound AT (2.0 ml of a 10.3 mg in 10 ml of toluene solution) were added to the reactor. The reactor was heated at 80° C., the ethylene was introduced (65 psi), and the reaction was allowed to run for 10 minutes, followed by rapidly cooling and venting the system. After evaporation of the toluene, 46.0 g of an ethylene-propylene copolymer was recovered (MW=110,200, MWD=5.489, 20 wt% ethylene by IR).

EXAMPLE 46

Polymerization—Compound AT

Using the same reactor design and general procedure described in Example 40, 300 ml of toluene, 100 ml of 1-butene, 7.0 ml of 1.0M MAO, and 1.03 mg of compound AT (1.0 ml of a 10.3 mg in 10 ml of toluene solution) were added to the reactor. The reactor was heated at 80° C., the ethylene was introduced (65 psi), and the reaction was allowed to run for 10 minutes, followed by rapidly cooling and venting the system. After evaporation of the toluene, 35.1 g of an ethylene-1-butene copolymer was recovered (MW=94,400, MWD=2.405, 165 SCB/1000C by $^{13}$C NMR).

EXAMPLE 47

Polymerization—Compound AT

Using the same reactor design and general procedure described in Example 40, 300 ml of toluene, 100 ml of 1-octene, 7.0 ml of 1.0M MAO, and 1.04 mg of compound AT (1.0 ml of a 10.4 mg in 10 ml of toluene solution) were added to the reactor. The reactor was heated at 80° C., the ethylene was introduced (65 psi), and the reaction was allowed to run for 10 minutes, followed by rapidly cooling and venting the system. After evaporation of the toluene, 30.6 g of an ethylene-1-octene copolymer was recovered (MW=73,100, MWD=2.552, 77.7 SCB/1000C by $^{13}$C NMR).

EXAMPLE 48

Polymerization—Compound BT

Using the same reactor design and general procedure described in Example 40, 400 ml of toluene, 5.0 ml of 1.0M MAO, and 0.248 mg of compound BT (0.2 ml of a 12.4 mg in 10 ml of toluene solution) were added to the reactor. The reactor was heated at 80° C., the ethylene was introduced (60 psi), and the reaction was allowed to run for 10 minutes, followed by rapidly cooling and venting the system. After evaporation of the toluene, 3.8 g of polyethylene Was recovered (MW=451,400, MWD=3.692).

EXAMPLE 49

Polymerization—Compound CT

Using the same reactor design and general procedure described in Example 40, 400 ml of toluene, 5.0 ml of 1.0M MAO, and 0.234 mg of compound CT (0.2 ml of a 11.7 mg in 10 ml of toluene solution) were added to the reactor. The reactor was heated at 80° C., the ethylene was introduced (60 psi), and the reaction was allowed to run for 10 minutes, followed by rapidly cooling and venting the system. After evaporation of the toluene, 2.7 g of polyethylene was recovered (MW=529,100, MWD=3.665).

EXAMPLE 50

Polymerization—Compound DT

Using the same reactor design and general procedure described in Example 40, 400 ml of toluene, 5.0 ml of 1.0M MAO, and 0.28 mg of compound DT (0.2 ml of a 14.0 mg in 10 ml of toluene solution) were added to the reactor. The reactor was heated at 80° C., the ethylene was introduced (60 psi), and the reaction was allowed to run for 10 minutes, followed by rapidly cooling and venting the system. After evaporation of the toluene, 9.0 g of polyethylene was recovered (MW=427,800, MWD=3.306).

EXAMPLE 51

Polymerization—Compound DT

Using the same reactor design and general procedure described in Example 40, 300 ml of toluene, 100 ml propylene, 7.0 ml of 1.0M MAO, and 1.4 mg of compound DT (1.0 ml of a 14.0 mg in 10 ml of toluene solution) were added to the reactor. The reactor was heated at 30° C. and the reaction was allowed to run for 1 hour, followed by rapidly cooling and venting the system. After evaporation of the toluene, 15 g of amorphous polypropylene was recovered (MW=18,600, MWD=1.657).

EXAMPLE 52

Polymerization—Compound ET

Using the same reactor design and general procedure described in Example 40, 300 ml of toluene, 100 ml 1-hexene, 70 ml of 1.0 M MAO, and 1.0 mg of compound ET (1.0 ml of a 10.0 mg in 10 ml of toluene solution) were added to the reactor. The reactor was heated at 80° C. and the ethylene was introduced (65 psi). During the polymerization, the reactor temperature increased by 20° C. After 10 minutes, the reactor was rapidly cooled and vented. After evaporation of the toluene, 106 g of an ethylene-1-hexene copolymer was recovered (MW=17,900, MWD=2.275, 39.1 SCB/1000C by NMR).

EXAMPLE 53

Polymerization—Compound AT

The polymerization was performed in a stirred 100 ml stainless steel autoclave which was equipped to perform polymerizations at temperatures up to 300° C. and pressures up to 2500 bar. The reactor was evacuated, purged with nitrogen, purged with ethylene and heated to 200° C. 1-hexene (75 ml) was added to the reactor under ethylene pressure. A stock solution of compound AT was prepared by dissolving 6.5 mg of compound AT in 12.5 ml of toluene. The test solution was prepared by adding 1.0 ml of the compound AT stock solution to 1.9 ml of 1.0M MAO solution, followed by 7.1 ml of toluene. The test solution (0.43 ml) was transferred by nitrogen pressure into a constant-volume injection tube. The autoclave was pressurized with ethylene to 1748 bar and was stirred at 1800 rpm. The test solution was injected into the autoclave with excess pressure, at which time a temperature rise of 16° C. was observed. The temperature and pressure were recorded continuously for 120 seconds, at which time the contents of the autoclave were rapidly vented into a receiving vessel. The reactor was washed with xylene to recover any polymer remaining within. These washings were combined with the polymer released when the reactor was vented. Precipitation of the polymer from the mixture by addition of acetone yielded 2.7 g of polymer (MW=64,000, MWD=3.16, 14.7 SCB/1000C by IR).

EXAMPLE 54

Polymerization—Compound AT

For this Example a stirred 1 L steel autoclave reaction vessel which was equipped to perform continuous Ziegler polymerization reactions at pressures to 2500 bar and temperatures up to 300° C. was used. The reaction system was supplied with a thermocouple and pressure transducer to measure temperature and pressure continuously, and with means to supply continuously purified compressed ethylene and 1-butene (or propylene). Equipment for continuously introducing a measured flow of catalysts solution, and equipment for rapidly venting and quenching the reaction, and of collecting the polymer product were also a part of the reaction system. The polymerization was performed with a molar ratio of ethylene to 1-butene of 1.6 without the addition of a solvent. The temperature of the cleaned reactor containing ethylene and 1-butene was equilibrated at the desired reaction temperature of 180° C. The catalyst solution was prepared by mixing 0.888 g of solid compound AT with 0.67 L of a 30 wt% methylalumoxane solution in 4.3 L of toluene in an inert atmosphere. This catalyst solution was continuously fed by a high pressure pump into the reactor at a rate of 0.56 L/hr which resulted in a temperature of 180° C. in the reactor. During this run, ethylene and 1-butene were pressured into the autoclave at a total pressure of 1300 bar. The reactor contents were stirred at 1000 rpm. The yield of polymer products was 3.9 kg/hr of an ethylene-1-butene copolymer which had a weight average molecular weight of 50,200, a molecular weight distribution of 2.36 and 60.1 SCB/1000C as measured by $^{13}$C NMR.

EXAMPLE 55

Polymerization—Compound AT

Using the same reactor design as described in Example 54, and using a molar ratio of ethylene to propylene of 2.6 without the addition of a solvent. The temperature of a cleaned reactor containing ethylene and propylene was equilibrated at the desired reaction temperature of 140° C. The catalyst solution was prepared by mixing 0.779 g of solid compound AT with 0.5 L of a 30 wt% methylalumoxane solution in 24.5 L of toluene in an inert atmosphere. This catalyst solution was continuously fed by a high pressure pump into the reactor at a rate of 0.9 L/hr which resulted in a temperature of 140° C. in the reactor. During this run, ethylene and propylene were pressured into the autoclave at a total pressure of 2200 bar. The reactor contents were stirred at 1000 rpm. The yield of polymer product was 2.3 kg/hr of an ethylene-propylene copolymer which had a weight average molecular weight of 102,700, a molecular weight distribution of 2.208 and a density of 0.863 g/cc.

EXAMPLE 56

Polymerization—Compound FT

Using the same reactor design as described in Example 54, and using a molar ratio of ethylene to 1-butene of 1.6 without the addition of a solvent. The temperature of the cleaned reactor containing ethylene and 1-butene was equilibrated at the desired reaction temperature of 180° C. The catalyst solution was prepared by mixing 0.859 g of solid FT with 30 wt% methylalumoxane solution and toluene such that the catalyst concentration was 0.162 g/L with an Al/M molar ratio of 1200. The preparation was done under an inert atmosphere. This catalyst solution was continuously fed by a high pressure pump into the reactor at a rate of 1.15 L/hr which resulted in a temperature of 180° C. in the reactor. During this run, ethylene and 1-butene were pressured into the autoclave at a total pressure of 1300. The reactor contents were stirred at 1000 rpm. The yield of polymer product was 3.9 kg/hr of an ethylene-1-butene copolymer which had a weight average molecular weight of 61,400, a molecular weight distribution of 2.607 and 104.8 SCB/1000C by $^{13}$C NMR.

EXAMPLE 57

Polymerization—Compound GT

Using the same reactor design and general procedure as described in Example 40, 300 ml of toluene, 100 ml of 1-hexene, 7.0 ml of 1.0M MAO, and 1.23 mg of compound GT (1.0 ml of a 12.3 mg in 10 ml of toluene solution) were added to the reactor. The reactor was heated at 80° C., and ethylene was introduced (65 psi), and the reaction was allowed to run for 30 minutes, followed by rapidly cooling and venting the system. After evaporation of the toluene, 47.2 g of an ethylene-1-hexene copolymer was recovered (MW=313,000, MWD=3.497, 41.0 SCB/1000C by $^{13}$C NMR.

EXAMPLE 58

Polymerization—Compound AT

Using the same reactor design as described in Example 54, and using a molar ratio of ethylene to 1-butene of 1.6 without the addition of a solvent, the temperature of the cleaned reactor containing ethylene and 1-butene was equilibrated at the desired reaction temperature of 170° C. The catalyst solution was prepared by mixing 0.925 g of solid compound AT with 2 L of a 10 wt% methylalumoxane solution in 8 L of toluene in an inert atmosphere. This catalyst solution was continuously fed by a high pressure pump into the reactor at a rate of 0.28 L/hr which resulted in a temperature of 170° C. in the reactor. During this run, ethylene and 1-butene were pressured into the autoclave at a total pressure of 1300 bar. The reactor contents were stirred at 1000 rpm. The yield of polymer product was 3.7 kg/hr of an ethylene-1-butene copolymer which had a weight average molecular weight of 69,500, a molecular weight distribution of 2.049 and 35.7 SCB/1000C by $^{13}$C NMR.

EXAMPLE 59

Polymerization—Compound BT

Using the same reactor design as described in Example 54, and using a molar ratio of ethylene to 1-butene of 1.6 without the addition of a solvent, the temperature of the cleaned reactor containing ethylene and 1-butene was equilibrated at the desired reaction temperature of 180° C. The catalyst solution was prepared by mixing 0.995 g of solid compound BT with 30 wt% methylalumoxane solution and toluene such that the catalyst concentration was 0.187 g/L and the Al/M molar ratio was 1300. The preparation was done under an inert atmosphere. This catalyst solution was continuously fed by a high pressure pump into the reactor at a rate of 1.0 L/hr which resulted in a temperature of 180° C. in the reactor. During this run, ethylene and 1-butene were pressured into the autoclave at a total pressure of 1300 bar. The reactor contents were stirred at 1000 rpm. The yield of polymer product was 3.9 kg/hr of an ethylene-1-butene copolymer which had a weight average molecular weight of 65,000, a molecular weight distribution of 2.623 and 55.5 SCB/1000C as measured by $^{13}$C NMR.

EXAMPLE 60

Polymerization—Compound H

Using the same reactor design as described in Example 54, and using a molar ratio of ethylene to 1-butene of 1.6 without the addition of a solvent, the temperature of the cleaned reactor containing ethylene and 1-butene was equilibrated at the desired reaction temperature of 180° C. The catalyst solution was prepared by mixing 1.94 g of solid compound H with 2.0 L of a 10 wt% methylalumoxane solution in 3 L of toluene in an inert atmosphere. This catalyst solution was continuously fed by a high pressure pump into the reactor at a rate of 1.5

L/hr which resulted in a temperature of 180° C. in the reactor. During this run, ethylene and 1-butene were pressured into the autoclave at a total pressure of 1300 bar. The reactor contents were stirred at 1000 rpm. The yield of polymer product was 3.9 kg/hr of an ethylene-1-butene copolymer which had a weight average molecular weight of 31,900 and 46.5 SCB/1000C as measured by $^{13}$C NMR.

EXAMPLE 61

Polymerization—Compound I

Using the same reactor design as described in Example 54, and using a molar ratio of ethylene to 1-butene of 1.6 without the addition of a solvent, the temperature of the cleaned reactor containing ethylene and 1-butene was equilibrated at the desired reaction temperature of 180° C. The catalyst solution was prepared by mixing 1.92 g of solid compound I with 2.0 L of a 10 wt% methylalumoxane solution in 3 L of toluene in an inert atmosphere. This catalyst solution was continuously fed by a high pressure pump into the reactor at a rate of 0.67 L/hr which resulted in a temperature of 180° C. in the reactor. During this run, ethylene and 1-butene were pressured into the autoclave at a total pressure of 1300 bar. The reactor contents were stirred at 1000 rpm. The yield of polymer product was 3.9 kg/hr of an ethylene-1-butene copolymer which had a weight average molecular weight of 40,800, a molecular weight distribution of 2.009 and 36.9 SCB/1000C as measured by $^{13}$C NMR.

EXAMPLE 62

Polymerization—Compound K

Using the same reactor design as described in Example 54, and using a molar ratio of ethylene to 1-butene of 1.6 without the addition of a solvent, the temperature of the cleaned reactor containing ethylene and 1-butene was equilibrated at the desired reaction temperature of 180° C. The catalyst solution was prepared by mixing 1.80 g of solid compound K with 2.0 L of a 10 wt% methylalumoxane solution in 3 L of toluene in an inert atmosphere. This catalyst solution was continuously fed by a high pressure pump into the reactor at a rate of 1.7 L/hr which resulted in a temperature of 180° C. in the reactor. During this run, ethylene and 1-butene were pressured into the autoclave at a total pressure of 1300 bar. The reactor contents were stirred at 1000 rpm. The yield of polymer product was 3.9 kg/hr of an ethylene-1-butene copolymer which had a weight average molecular weight of 51,700, a molecular weight distribution of 1.532 and 30.1 SCB/1000C as measured by $^{13}$C NMR.

EXAMPLE 63

Polymerization—Compound L

Using the same reactor design as described in Example 54, and using a molar ratio of ethylene to 1-butene of 1.6 without the addition of a solvent, the temperature of the cleaned reactor containing ethylene and b 1-butene was equilibrated at the desired reaction temperature of 180° C. The catalyst solution was prepared by mixing 1.95 g of solid compound L with 2.0 L of a 10 wt% methylalumoxane solution in 3 L of toluene in an inert atmosphere. This catalyst solution was continuously fed by a high pressure pump into the reactor at a rate of 1.2 L/hr which resulted in a temperature of 180° C. in the reactor. During this run, ethylene and 1-butene were pressured into the autoclave at a total pressure of 1300 bar. The reactor contents were stirred at 1000 rpm. The yield of polymer product was 3.9 kg/hr of an ethylene-1-butene copolymer which had a weight average molecular weight of 38,800, a molecular weight distribution of 1.985 and 39.3 SCB/1000C as measured by $^{13}$C NMR.

EXAMPLE 64

Polymerization—Compound HT

Using the same reactor design as described in Example 54, and using a molar ratio of ethylene to 1-butene of 1.6 without the addition of a solvent, the temperature of the cleaned reactor containing ethylene and i-butene was equilibrated at the desired reaction temperature of 180° C. The catalyst solution was prepared by mixing 2.01 g of solid compound HT with 30 wt% methylalumoxane solution and toluene such that the catalyst concentration was 0.354 g/L and the Al/M molar ratio was 400. The preparation was done under an inert atmosphere. This catalyst solution was continuously fed by a high pressure pump into the reactor at a rate of 1.15 L/hr which resulted in a temperature of 180° C. in the reactor. During this run, ethylene and 1-butene were pressured into the autoclave at a total pressure of 1300 bar. The reactor contents were stirred at 1000 rpm. The yield of polymer product was 3.9 kg/hr of an ethylene-1-butene copolymer which had a weight average molecular weight of 61,700, a molecular weight distribution of 2.896 and 62.9 SCB/1000C as measured by $^{13}$C NMR.

EXAMPLE 65

Polymerization—Compound F

Using the same reactor design as described in Example 54, and using a molar ratio of ethylene to 1-butene of 1.6 without the addition of a solvent, the temperature of the cleaned reactor containing ethylene and 1-butene was equilibrated at the desired reaction temperature of 180° C. The catalyst solution was prepared by mixing 1.31 g of solid compound F with 2.0 L of a 10 wt% methylalumoxane solution in 3 L of toluene in an inert atmosphere. This catalyst solution was continuously fed by a high pressure pump into the reactor at a rate of 0.56 L/hr which resulted in a temperature of 180° C. in the reactor. During this run, ethylene and 1-butene were pressured into the autoclave at a total pressure of 1300 bar. The reactor contents were stirred at 1000 rpm. The yield of polymer product was 3.9 kg/hr of an ethylene-1-butene copolymer which had a weight average molecular weight of 43,400, a molecular weight distribution of 2.001 and 40.1 SCB/1000C as measured by $^{13}$C NMR.

EXAMPLE 66

Polymerization—Compound G

Using the same reactor design as described in Example 54, and using a molar ratio of ethylene to 1-butene of 1.6 without the addition of a solvent, the temperature of the cleaned reactor containing ethylene and 1-butene was equilibrated at the desired reaction temperature of 180° C. The catalyst solution was prepared by mixing 1.53 g of solid compound G with 0.5 L of a 30 wt% methylalumoxane solution in 4.5 L of toluene in an inert atmosphere. This catalyst solution was continuously fed by a high pressure pump into the reactor at a rate of 0.58

L/hr which resulted in a temperature of 180° C. in the reactor. During this run, ethylene and 1-butene were pressured into the autoclave at a total pressure of 1300 bar. The reactor contents were stirred at 1000 rpm. The yield of polymer product was 3.9 kg/hr of an ethylene-1-butene copolymer which had a weight average molecular weight of 47,400, a molecular weight distribution of 2.198 and 37.6 SCB/1000C as measured by $^{13}C$ NMR.

EXAMPLE 67

Polymerization—Compound IT

Using the same reactor design as described in Example 54, and using a molar ratio of ethylene to 1-butene of 1.6 without the addition of a solvent, the temperature of the cleaned reactor containing ethylene and 1-butene was equilibrated at the desired reaction temperature of 180° C. The catalyst solution was prepared by mixing 1.94 g of solid compound IT with 30 wt% methylalumoxane solution and toluene such that the catalyst concentration was 0.388 g/L and the Al/M molar ratio was 600. The preparation was done under an inert atmosphere. This catalyst solution was continuously fed by a high pressure pump into the reactor at a rate of 0.42 L/hr which resulted in a temperature of 180° C. in the reactor. During this run, ethylene and 1-butene were pressured into the autoclave at a total pressure of 1300 bar. The reactor contents were stirred at 1000 rpm. The yield of polymer product was 3.9 kg/hr of an ethylene-1-butene copolymer which had a weight average molecular weight of 50,800, a molecular weight distribution of 2.467 and 69 SCB/1000C as measured by $^1H$ NMR.

EXAMPLE 68

Polymerization—Compound A

Using the same reactor design as described in Example 54, and using a molar ratio of ethylene to 1-butene of 1.6 without the addition of a solvent, the temperature of the cleaned reactor containing ethylene and 1-butene was equilibrated at the desired reaction temperature of 180° C. The catalyst solution was prepared by mixing 1.95 g of solid compound A with 0.67 L of a 30 wt% methylalumoxane solution in 4.3 L of toluene in an inert atmosphere. This catalyst solution was continuously fed by a high pressure pump into the reactor at a rate of 0.4 L/hr which resulted in a temperature of 180° C. in the reactor. During this run, ethylene and 1-butene were pressured into the autoclave at a total pressure of 1300 bar. The reactor contents were stirred at 1000 rpm. The yield of polymer products was 3.9 kg/hr of an ethylene-1-butene copolymer which had a weight average molecular weight of 71,100, a molecular weight distribution of 1.801 and 12.4 SCB/1000C as measured by $^{13}C$ NMR.

EXAMPLE 69

Polymerization—Compound B

Using the same reactor design as described in Example 54, and using a molar ratio of ethylene to 1-butene of 1.6 without the addition of a solvent, the temperature of the cleaned reactor containing ethylene and 1-butene was equilibrated at the desired reaction temperature of 180° C. The catalyst solution was prepared by mixing 1.97 g of solid compound B with 0.67 L of a 30 wt% methylalumoxane solution in 4.3 L of toluene in an inert atmosphere. This catalyst solution was continuously fed by a high pressure pump into the reactor at a rate of 0.35 L/hr which resulted in a temperature of 180° C. in the reactor. During this run, ethylene and 1-butene were pressured into the autoclave at a total pressure of 1300 bar. The reactor contents were stirred at 1000 rpm. The yield of polymer product was 3.9 kg/hr of an ethylene-1-butene copolymer which has a weight average molecular weight of 47,300, and a molecular weight distribution of 2.056 and 34.1 SCB/1000C as measured by $^{13}C$ NMR.

EXAMPLE 70

Polymerization—Compound JT

Using the same reactor design as described in Example 54, and using a molar ratio of ethylene to 1-butene of 1.6 without the addition of a solvent, the temperature of the cleaned reactor containing ethylene and 1-butene was equilibrated at the desired reaction temperature of 180° C. The catalyst solution was prepared by mixing 1.78 g of solid compound JT with 30 wt% methylalumoxane solution and toluene such that the catalyst concentration was 0.318 g/L and the Al/M molar ratio was 1400. The preparation was done under an inert atmosphere. This catalyst solution was continuously fed by a high pressure pump into the reactor at a rate of 0.55 L/hr which resulted in a temperature of 180° C. in the reactor. During thus run, ethylene and 1-butene were pressured into the autoclave at a total pressure of 1300 bar. The reactor contents were stirred at 1000 rpm. The yield of polymer product was 3.9 kg/hr of an ethylene-1-butene copolymer which had a weight average molecular weight of 72,600, a molecular weight distribution of 2.385 and 110 SCB/1000C as measured by $^1H$ NMR.

Table 2 summarizes the polymerization conditions employed and the properties obtained in the product polymers as set forth in Examples 1-39 above.

TABLE 2

| EXP. NO. | DILUENT Type | DILUENT ml | TRANSITION METAL COMPOUND (TMC) Type | TRANSITION METAL COMPOUND (TMC) mmole | ALUMOXANE Type | ALUMOXANE mmole | mmole MAO:TMC (× 10³) | MONOMER | CO-MONOMER | RXN. TEMP. °C. | RXN. TIME HR. | YIELD g. | MW | MWD | SCB/1000 C NMR | SCB/1000 C IR | CAT. ACTIVITY G. POLYMER/MMOLE TMC-HOUR |
|---|---|---|---|---|---|---|---|---|---|---|---|---|---|---|---|---|---|
| 4 | Hexane | 300 | A | 5.588 × 10⁻⁴ | MAO | 9 | 16.11 | ethylene-60 psi | | 80 | 0.5 | 5.4 | 212,600 | 2.849 | | | 1.933 × 10⁴ |
| 1 | Toluene | 400 | A | 5.588 × 10⁻⁴ | MAO | 9 | 16.11 | ethylene-60 psi | | 80 | 0.5 | 9.2 | 257,200 | 2.275 | | | 3.293 × 10⁴ |
| 2 | Toluene | 300 | A | 2.794 × 10⁻⁴ | MAO | 4.5 | 16.11 | ethylene-60 psi | | 80 | 0.5 | 3.8 | 359,800 | 2.425 | | | 2.720 × 10⁴ |
| 3 | Toluene | 300 | A | 2.794 × 10⁻⁴ | MAO | 4.5 | 16.11 | ethylene-60 psi | | 40 | 0.5 | 2.4 | 635,000 | 3.445 | | | 1.718 × 10⁴ |
| 16 | Toluene | 400 | A | 5.588 × 10⁻⁴ | MAO | 5 | 8.95 | ethylene-400 psi | | 80 | 0.5 | 19.4 | 343,700 | 3.674 | | | 6.943 × 10⁴ |
| 12 | Toluene | 400 | Aᵃ | 5.588 × 10⁻⁴ | MAO | 5.02 | 8.98 | ethylene-60 psi | | 80 | 0.5 | 3.4 | 285,000 | 2.808 | | | 1.217 × 10⁴ |
| 13 | Toluene | 400 | Aᵃ,ᵇ | 5.588 × 10⁻⁴ | MAO | 5.02 | 8.98 | ethylene-60 psi | | 80 | 0.5 | 2.0 | 260,700 | 2.738 | | | 7.158 × 10³ |
| 14 | Toluene | 400 | Aᵃ | 5.588 × 10⁻⁴ | MAO | 0.26 | 0.47 | ethylene-60 psi | | 80 | 0.5 | 1.1 | 479,600 | 3.130 | | | 3.937 × 10³ |
| 15 | Toluene | 400 | Aᵃ | 5.588 × 10⁻⁴ | MAO | 0.1 | 0.018 | ethylene-60 psi | | 80 | 0.5 | 1.6 | 458,800 | 2.037 | | | 5.727 × 10² |
| 18 | Toluene | 400 | B | 5.573 × 10⁻⁴ | MAO | 5 | 8.97 | ethylene-60 psi | | 80 | 0.17 | 9.6 | 241,200 | 2.628 | | | 1.034 × 10⁵ |
| 19 | Toluene | 300 | C | 1.118 × 10⁻³ | MAO | 4 | 3.58 | ethylene-60 psi | | 80 | 0.5 | 1.7 | 278,400 | 2.142 | | | 3.041 × 10³ |
| 20 | Toluene | 400 | D | 5.573 × 10⁻⁴ | MAO | 5 | 8.97 | ethylene-60 psi | | 80 | 0.5 | 1.9 | 229,700 | 2.618 | | | 6.819 × 10³ |
| 21 | Hexane | 300 | E | 5.61 × 10⁻⁴ | MAO | 9 | 16.04 | ethylene-60 psi | | 80 | 0.5 | 2.2 | 258,200 | 2.348 | | | 7.843 × 10³ |
| 23 | Toluene | 400 | F | 4.79 × 10⁻⁴ | MAO | 5 | 10.44 | ethylene-60 psi | | 80 | 0.5 | 5.3 | 319,900 | 2.477 | | | 2.213 × 10⁴ |
| 25 | Toluene | 400 | G | 5.22 × 10⁻⁴ | MAO | 5 | 9.58 | ethylene-60 psi | | 80 | 0.5 | 3.5 | 237,300 | 2.549 | | | 1.341 × 10⁴ |
| 27 | Toluene | 400 | H | 5.62 × 10⁻⁴ | MAO | 5 | 8.90 | ethylene-60 psi | | 80 | 0.5 | 11.1 | 299,800 | 2.569 | | | 3.950 × 10⁴ |
| 29 | Toluene | 400 | I | 5.57 × 10⁻⁴ | MAO | 5 | 8.98 | ethylene-60 psi | | 80 | 0.5 | 0.9 | 377,000 | 1.996 | | | 3.232 × 10³ |
| 30 | Toluene | 400 | J | 5.59 × 10⁻⁴ | MAO | 5 | 8.94 | ethylene-60 psi | | 80 | 0.5 | 8.6 | 321,000 | 2.803 | | | 3.077 × 10⁴ |
| 32 | Toluene | 300 | K | 5.06 × 10⁻⁴ | MAO | 5 | 9.87 | ethylene-60 psi | | 80 | 0.5 | 26.6 | 187,300 | 2.401 | | | 1.051 × 10⁵ |
| 34 | Toluene | 400 | L | 5.60 × 10⁻⁴ | MAO | 5 | 8.93 | ethylene-60 psi | | 80 | 0.5 | 15.5 | 174,300 | 2.193 | | | 5.536 × 10⁴ |
| 5 | Toluene | 300 | A | 1.118 × 10⁻³ | MAO | 9 | 8.05 | ethylene-60 psi | propylene-200 ml | 80 | 0.5 | 13.3 | 24,900 | 2.027 | | 73.5 | 2.379 × 10⁴ |
| 6 | Toluene | 200 | A | 2.235 × 10⁻³ | MAO | 9 | 4.03 | ethylene-60 psi | propylene-200 ml | 50 | 0.5 | 6.0 | 83,100 | 2.370 | | 75.7 | 5.369 × 10³ |
| 7 | Toluene | 150 | A | 5.588 × 10⁻⁴ | MAO | 9 | 1.61 | ethylene-65 psi | 1-butene-100 ml | 50 | 0.5 | 25.4 | 184,500 | 3.424 | 23.5 | 21.5 | 9.091 × 10⁵ |
| 8 | Toluene | 100 | A | 5.588 × 10⁻⁴ | MAO | 9 | 1.61 | ethylene-65 psi | 1-butene-150 ml | 50 | 0.5 | 30.2 | 143,400 | 3.097 | 30.8 | 26.5 | 1.081 × 10⁴ |
| 9 | Toluene | 200 | A | 5.588 × 10⁻⁴ | MAO | 8 | 1.43 | ethylene-60 psi | 1-butene | 50 | 0.5 | 24.9 | 163,200 | 3.290 | 23.3 | 18.9 | 8.912 × 10³ |

TABLE 2-continued

| EXP. NO. | DILUENT Type | ml | TRANSITION METAL COMPOUND (TMC) Type | mmole | ALUMOXANE Type | mmole | mmole MAO:TMC (× 10³) | MONO-MER | CO-MONOMER | RXN. TEMP. °C. | RXN. TIME HR. | YIELD g. | MW | MWD | SCB/1000 C NMR | SCB/1000 C IR | CAT. ACTIVITY G. POLYMER/ MMOLE TMC-HOUR |
|---|---|---|---|---|---|---|---|---|---|---|---|---|---|---|---|---|---|
| 10 | Hexane | 200 | A | 5.588 × 10⁻³ | MAO | 8 | 1.43 | ethylene-65 psi | 1-butene-50 ml | 50 | 0.5 | 19.5 | 150,600 | 3.150 | 12.1 | 12.7 | 6.979 × 10³ |
| 11 | Hexane | 150 | A | 5.588 × 10⁻³ | MAO | 8 | 1.43 | ethylene-65 psi | 1-butene-50 ml | 50 | 0.5 | 16.0 | 116,200 | 3.510 | 19.2 | 19.4 | 5.727 × 10³ |
| 22 | Toluene | 200 | E | 5.61 × 10⁻³ | MAO | 9 | 1.60 | ethylene-65 psi | 1-butene-100 ml | 50 | 0.5 | 1.8 | 323,600 | 2.463 | | 33.5 | 6.417 × 10² |
| 24 | Toluene | 150 | F | 4.79 × 10⁻³ | MAO | 9 | 1.88 | ethylene-65 psi | 1-butene-100 ml | 50 | 0.5 | 3.5 | 251,300 | 3.341 | | 33.3 | 1.461 × 10³ |
| 26 | Toluene | 150 | G | 5.22 × 10⁻³ | MAO | 7 | 1.34 | ethylene-65 psi | 1-butene-100 ml | 50 | 0.5 | 7.0 | 425,000 | 2.816 | | 27.1 | 2.682 × 10³ |
| 28 | Toluene | 150 | H | 5.62 × 10⁻³ | MAO | 7 | 1.25 | ethylene-65 psi | 1-butene-100 ml | 50 | 0.5 | 15.4 | 286,600 | 2.980 | | 45.4 | 5.480 × 10³ |
| 30 | Toluene | 150 | J | 5.59 × 10⁻³ | MAO | 7 | 1.25 | ethylene-65 psi | 1-butene-100 ml | 50 | 0.5 | 11.2 | 224,800 | 2.512 | | 49.6 | 4.007 × 10³ |
| 32 | Toluene | 150 | K | 5.06 × 10⁻³ | MAO | 7 | 1.38 | ethylene-65 psi | 1-butene-100 ml | 50 | 0.5 | 3.9 | 207,600 | 2.394 | | 33.9 | 1.542 × 10³ |
| 35 | Toluene | 250 | A | 5.588 × 10⁻³ | MAO | 7 | 1.25 | ethylene-65 psi | 1-hexene-100 ml | 50 | 0.5 | 26.5 | 222,800 | 3.373 | | 39.1 | 9.485 × 10³ |
| 36 | Toluene | 300 | A | 5.588 × 10⁻³ | MAO | 7 | 1.25 | ethylene-65 psi | 1-octene-150 ml | 50 | 0.5 | 19.7 | 548,600 | 3.007 | | 16.5 | 6.979 × 10³ |
| 37 | Toluene | 300 | A | 5.588 × 10⁻³ | MAO | 7 | 1.25 | ethylene-65 psi | 4-methyl-1-pentene-100 ml | 50 | 0.5 | 15.1 | 611,800 | 1.683 | | 1.8ᶜ | 5.404 × 10³ |
| 38 | Toluene | 300 | A | 5.588 × 10⁻³ | MAO | 7 | 1.25 | ethylene-65 psi | norhornene-100 ml 2.2M | 50 | 0.5 | 12.3 | 812,600 | 1.711 | | 0.3ᶜ | 4.402 × 10³ |
| 39 | Toluene | 300 | A | 5.588 × 10⁻³ | MAO | 7 | 1.25 | ethylene-65 psi | cis-1,4-hexadiene 100 ml | 50 | 0.5 | 13.6 | 163,400 | 2.388 | | 2.2ᶜ | 4.868 × 10³ |

ᵃCompound A was preactivated by dissolving the compound in solvent containing MAO.
ᵇPreincubation of activated compound A was for one day.
ᶜMole % comonomer.

Tables A, B, and C summarize the polymerization conditions employed and the properties obtained in the polymer products of Example Nos. 40-50, 52, 54-59, 64, 67 and 70 wherein a titanium species of Group IV B metal component is employed in the catalyst system.

Table D summarizes the condition employed and properties obtained in the polymer products produced by catalyst systems wherein each Group IV B metal is the species of a monocyclopentadienyl compound which is otherwise of identical structure except for the identity of the Group IV B metal itself.

TABLE A

| Example Number | Transition Metal Compound (TMC) Type | Transition Metal Compound (TMC) mmole | Methyl-alumoxane (MAO) mmole | mmole MAO:TMC ($\times 10^3$) | Ethylene Pressure (psi) | Rxn Temp. °C. | Rxn Time hr. | Yield g | MW | MWD | Cat Activity g poly/mmole TMC-HR |
|---|---|---|---|---|---|---|---|---|---|---|---|
| 41[a] | AT | $4.79 \times 10^{-4}$ | 5.01 | 10.5 | 60 | 80 | 0.5 | 14.5 | 406,100 | 2.486 | $6.05 \times 10^4$ |
| 40 | AT | $4.79 \times 10^{-4}$ | 5 | 10.4 | 60 | 80 | 0.5 | 11.8 | 279,700 | 2.676 | $4.93 \times 10^4$ |
| 50 | DT | $5.59 \times 10^{-4}$ | 5 | 8.94 | 60 | 80 | 0.166 | 9.0 | 427,800 | 3.306 | $9.70 \times 10^4$ |
| 48 | BT | $5.58 \times 10^{-4}$ | 5 | 8.96 | 60 | 80 | 0.166 | 3.8 | 451,400 | 3.692 | $4.10 \times 10^4$ |
| 49 | CT | $5.59 \times 10^{-4}$ | 5 | 8.94 | 60 | 80 | 0.166 | 2.7 | 529,100 | 3.665 | $2.91 \times 10^4$ |

[a]Transition metal compound was preactivated before polymerization by admixing it with a quantity of methylalumoxane sufficient to provide a MAO:TMC ratio of 20.9.

TABLE B

| Example Number | Transition Metal Compound (TMC) Type | Transition Metal Compound (TMC) mmole | Methyl-alumoxane (MAO) mmole | mmole MAO:TMC ($\times 10^3$) | Ethylene Pressure (psi) | Co-monomer Amount | Rxn. Temp. °C. | Rxn. Time hr. | Yield g | MW | MWD | SCB/ 1000 C[c] | Cat g Poly/ mmole TMC-HR |
|---|---|---|---|---|---|---|---|---|---|---|---|---|---|
| 45 | AT | $4.79 \times 10^{-3}$ | 7 | 1.46 | 65 | Propylene: 100 ml | 80 | 0.166 | 46.0 | 110,200 | 5.489 | (Propylene)[b] 80 wt % | $5.79 \times 10^4$ |
| 46 | AT | $2.39 \times 10^{-3}$ | 7 | 2.93 | 65 | 1-Butene: 100 ml | 80 | 0.166 | 35.1 | 94,400 | 2.405 | 165 | $8.85 \times 10^4$ |
| 44 | AT | $2.39 \times 10^{-3}$ | 7 | 2.93 | 65 | 1-Hexene: 25 ml | 50 | 0.166 | 15.0 | 310,000 | 2.579 | 47.2 | $3.78 \times 10^4$ |
| 43 | AT | $2.39 \times 10^{-3}$ | 7 | 2.93 | 65 | 1-Hexene: 25 ml | 80 | 0.166 | 29.2 | 129,800 | 2.557 | 53.0 | $7.36 \times 10^4$ |
| 42 | AT | $2.39 \times 10^{-3}$ | 7 | 2.93 | 65 | 1-Hexene: 100 ml | 80 | 0.166 | 48.6 | 98,500 | 1.745 | 117 | $1.22 \times 10^5$ |
| 52 | ET | $2.76 \times 10^{-3}$ | 7 | 2.54 | 65 | 1-Hexene: 100 ml | 80[d] | 0.166 | 106 | 17,900 | 2.275 | 39.1 | $2.31 \times 10^5$ |
| 57 | GT | $2.81 \times 10^{-3}$ | 7 | 2.49 | 65 | 1-Hexene: 100 ml | 80 | 0.5 | 47.2 | 313,000 | 3.497 | 41.0 | $3.36 \times 10^4$ |
| 47 | AT | $2.42 \times 10^{-3}$ | 7 | 2.89 | 65 | 1-Octene: 100 ml | 80 | 0.166 | 30.6 | 73,100 | 2.552 | 77.7 | $7.62 \times 10^4$ |

[b]Determined by IR
[c]Determined by $^{13}$C NMR
[d]During polymerization the reactor temperature increased by 20° C.

TABLE C

| Example Number | Transition Metal Compound (TMC) | AL: TMC | Catalyst TMC Feed Rate (mmole/hr) | Co-monomer (Com) | Ethylene/ Com Mole Ratio | Rxn. Pressure (bar) | Rxn. Temp °C. | Yield (kg/hr) | MW | MWD | SCB/[f] 1000 C | Cat. Activity kg Polymer/ mmol TMC |
|---|---|---|---|---|---|---|---|---|---|---|---|---|
| 55[e] | AT | 1200 | 1.63 | Propylene | 2.6 | 2200 | 140 | 2.3 | 102,700 | 2.208 | 127.7 | 1.4 |
| 54 | AT | 1500 | 0.231 | 1-Butene | 1.6 | 1300 | 180 | 3.9 | 50,200 | 2.36 | 60.1 | 16.9 |
| 67 | IT | 600 | 0.442 | 1-Butene | 1.6 | 1300 | 180 | 3.9 | 50,800 | 2.467 | 69[g] | 8.8 |
| 64 | HT | 400 | 1.05 | 1-Butene | 1.6 | 1300 | 180 | 3.9 | 61,700 | 2.896 | 62.9 | 3.7 |
| 59 | BT | 1300 | 0.421 | 1-Butene | 1.6 | 1300 | 180 | 3.9 | 65,000 | 2.623 | 55.5 | 9.3 |
| 58 | AT | 1400 | 0.060 | 1-Butene | 1.6 | 1300 | 170 | 3.7 | 69,500 | 2.049 | 35.7 | 61.7 |
| 56 | FT | 1200 | 0.366 | 1-Butene | 1.6 | 1300 | 180 | 3.9 | 61,400 | 2.607 | 104.8 | 8.3 |
| 70 | JT | 1400 | 0.366 | 1-Butene | 1.6 | 1300 | 180 | 3.9 | 72,600 | 2.385 | 110[g] | 10.7 |

[e]the polymer product had a density of 0.863 g/cc.
[f]Excepted where othrwise indicated, determined by $^{13}$CNMR.
[g]Determined by $^1$H NMR.

TABLE D

| Example Number | Transiton Metal Compound (TMC) | TM | Catalyst TMC Feal Rate mmole/hr | Cat. Activity[h] kg Polymer/ mmol TMC | MW | MWD | SCB/1000 C | r1 |
|---|---|---|---|---|---|---|---|---|
| 54 | AT | Ti | 0.23 | 17.0 | 50,200 | 2.360 | 60.1 | 10.1 |
| 60 | H | Zr | 1.23 | 3.2 | 31,900 | 12.070 | 46.6 | 14.1 |
| 61 | I | Hf | 0.42 | 9.3 | 40,800 | 2.009 | 36.9 | 18.4 |
| 59 | BT | Ti | 0.42 | 9.3 | 65,000 | 2.623 | 55.5 | 11.2 |
| 62 | K | Zr | 1.25 | 3.1 | 51,700 | 1.532 | 30.1 | 23.4 |
| 63 | L | Hf | 0.81 | 4.8 | 1.15 | 1.985 | 39.3 | 17.2 |
| 64 | HT | Ti | 1.05 | 3.7 | 61,700 | 2.896 | 62.9 | 9.5 |

TABLE D-continued

| Example Number | Transiton Metal Compound (TMC) | TM | Catalyst TMC Feal Rate mmole/hr | Cat. Activity[h] kg Polymer/ mmol TMC | MW | MWD | SCB/1000 C | r1 |
|---|---|---|---|---|---|---|---|---|
| 65 | F | Zr | 0.34 | 11.5 | 43,400 | 2.001 | 40.1 | 16.8 |
| 66 | G | Hf | 0.34 | 11.5 | 47,400 | 2.198 | 37.6 | 18.1 |
| 67 | IT | Ti | 0.44 | 8.9 | 50,800 | 2.467 | 69 | 8.4 |
| 68 | A | Zr | 0.38 | 10.3 | 71,100 | 1.801 | 12.4 | 59.9 |
| 69 | B | Hf | 0.69 | 5.7 | 47,300 | 2.056 | 34.1 | 20.3 |

[h]Polymer yield was 3.90 kg/hr.

It may be seen that the requirement for the alumoxane component can be greatly diminished by premixing the catalyst with the alumoxane prior to initiation of the polymerization (see Examples 12 through 15).

By appropriate selection of (1) Group IV B transition metal component for use in the catalyst system; (2) the type and amount of alumoxane used; (3) the polymerization diluent type and volume; (4) reaction temperature; and (5) reaction pressure, one may tailor the product polymer to the weight average molecular weight value desired while still maintaining the molecular weight distribution to a value below about 4.0.

The preferred polymerization diluents for practice of the process of the invention are aromatic diluents, such as toluene, or alkanes, such as hexane.

From the above examples it appears that for a catalyst system wherein the group IV B transition metal component is a titanium species of the following structure:

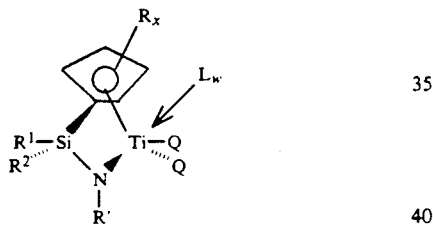

the nature of the R' group may dramatically influence the catalytic properties of the system. For production of ethylene-α-olefin copolymers of greatest comonomer content, at a selected ethylene to α-olefin monomer ratio, R' is preferably a non-aromatic substituent, such as an alkyl or cycloalkyl substituent preferably bearing as primary or secondary carbon atom attached to the nitrogen atom.

Further, from the above data, the nature of the Cp ligand structure of a Ti metal component may be seen to influence the properties of the catalyst system. Those Cp ligands which are not too sterically hindered and which contain good electron donor groups, for example the $Me_4C_5$ ligand, are preferred.

The resins that are prepared in accordance with this invention can be used to make a variety of products including films and fibers.

The invention has been described with reference to its preferred embodiments. Those of ordinary skill in the art may, upon reading this disclosure, appreciate changes or modifications which do not depart from the scope and spirit of the invention as described above or claimed hereafter.

I claim:

1. A catalyst system comprising:
   A) a Group IV B transition metal component of the formula:

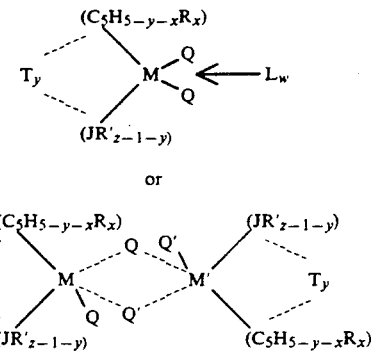

wherein

M is Ti in its highest formal oxidation state:

$(C_5H_{5-y-x}R_x)$ is a cyclopentadienyl ring which is substituted with from zero to five substituent groups R, "x" is 0, 1, 2, 3, 4 or 5 denoting the degree of substitution, and each substituent group R is, independently, a radical selected from a group consisting of $C_1$–$C_{20}$ hydrocarbyl radicals; substituted $C_1$–$C_{20}$ hydrocarbyl radicals wherein one or more hydrogen atoms is replaced by a halogen radical, an amido radical, a phosphido radical, an alkoxy radical or a radical containing a Lewis acidic or basic functionality; $C_1$–$C_{20}$ hydrocarbyl-substituted metalloid radicals wherein the metalloid is selected from the Group IV A of the Periodic Table of Elements; and halogen radicals, amido radicals, phosphido radicals, alkoxy radicals, alkylborido radicals, or a radical containing Lewis acidic or basic funtionality; or $(C_5H_{5-y-x}R_x)$ is a cyclopentadienyl ring in which two adjacent R-groups are joined forming $C_4$–$C_{20}$ ring to give a saturated or unsaturated polycyclic cyclopentadienyl ligand;

$(JR'_{z-1-y})$ is a heteroatom ligand in which J is an element with a coordination number of three from Group V A or an element with a coordination number of two from Group VI A of the Periodic Table of Elements, each R' is, independently a radical selected from a group consisting of $C_1$–$C_{20}$ hydrocarbyl radicals, substituted $C_1$–$C_{20}$ hydrocarbyl radicals wherein one or more hydrogen atoms is replaced by a halogen radical; an amido radical, an alkylborido radical, a phosido radical, an alkoxy radical, or a radical containing a Lewis acidic or basic functionality; and "z" is the coordination number of the element J;

each Q is, independently, any univalent anionic ligand, provided that where Q is a hydrocarbyl such Q is different than the $(C_5H_{5-y-x}R_x)$ or both Q together are an alkylidene, a cyclometallated hydrocarbyl or a divalent anionic chelating ligand;

"y" is 0 or 1 when "w" is greater than 0; "y" is 1 when "w" is 0; when "y" is 1, T is a covalent bridging group containing a Group IV A or V A element;

L is a neutral Lewis base where "w" denotes a number from 0 to 3; and (B) an alumoxane.

2. The catalyst system of claim 1 wherein the heteroatom ligand group J element is nitrogen, phosphorous, oxygen or sulfur.

3. The catalyst system of claim 1 wherein Q is a halogen or hydrocarbyl radical.

4. The catalyst system of claim 2 wherein the heteroatom ligand group J element is nitrogen.

5. The catalyst system of claim 1 wherein the mole ratio of aluminum atom to transition metal atom is from 1:1 to about 20,000:1.

6. The catalyst system of claim 1 wherein said saturated or unsaturated polycyclic cyclopentadienyl ligand is selected from the group of indenyl, tetrahydroindenyl, fluorenyl or octahydrofluorenyl.

7. The catalyst system of claim 1 wherein said univalent anionic ligand is selected from the group of halide, hydride, a substituted or unsubstituted $C_1$-$C_{20}$ hydrocarbyl, alkoxide, aryloxide, amide, arylamide, phosphide or arylphosphide.

* * * * *

UNITED STATES PATENT AND TRADEMARK OFFICE
CERTIFICATE OF CORRECTION

PATENT NO. : 5,096,867
DATED : March 17, 1992
INVENTOR(S) : Jo Ann M. Canich

Page 1 of 9

It is certified that error appears in the above-indentified patent and that said Letters Patent is hereby corrected as shown below:

Column 3, line 28: please delete the formula "$(C_2H_{5-y-x}R_x)$" and substitute therefor -- $(C_5H_{5-y-x}R_x)$ --;

Column 3, line 30: please insert -- 1, -- after "0,";

Column 3, line 35: please delete the word "amid" and substitute therefor -- amido --;

Column 3, line 35: please delete the word "or" and substitute therefor -- an --;

Column 4, lines 28-29: please delete the formula "$R^4(R^5-Al-O)_m-AlR^6$" and substitute therefor -- $R^4(R^5-Al-O)_m-AlR^6_2$ --;

Column 5, line 32: please insert -- 1, -- after "0,";

Column 5, line 45: please delete the formula "$(C_5H_{5-Y-x}R_x)$" and substitute therefor -- $(C_5H_{5-y-x}R_x)$ --;

Column 7, line 14: please delete the word "hydrocarbon" and substitute therefor -- hydrocarbyl --;

UNITED STATES PATENT AND TRADEMARK OFFICE
CERTIFICATE OF CORRECTION

PATENT NO. : 5,096,867
DATED : March 17, 1992
INVENTOR(S) : Jo Ann M. Canich

It is certified that error appears in the above-indentified patent and that said Letters Patent is hereby corrected as shown below:

Column 7, line 15: please delete the word "hydrocarbon" and substitute therefor -- hydrocarbyl --;

Columns 7-8, Table 1, column headed "$(JR'_{z-1-y})$": please delete the term "$\underline{t}$-butylamide" and substitute therefor -- $\underline{t}$-butylamido --;

Columns 9-10, Table 1, column headed "T (when y = 1)": please delete the term "1,1.4.4-tetramethyldisilylethylene" (the last compound in the column) and substitute therefor -- 1,1,4,4-tetramethyldisilylethylene --;

Columns 9-10, Table 1, column headed "$(C_5H_{5-y-x}R_x)$": please delete the term "pentamethylcyclcopentadienyl" and substitute therefor -- pentamethylcyclopentadienyl --;

Column 10, lines 30-31: please delete the term "pentamethylcyclopentadienyldi-t-butylphosphinodimethyl" and substitute therefor -- pentamethylcyclopentadienyldi-t-butylphosphidodimethyl --;

UNITED STATES PATENT AND TRADEMARK OFFICE
CERTIFICATE OF CORRECTION

PATENT NO. : 5,096,867
DATED : March 17, 1992
INVENTOR(S) : Jo Ann M. Canich

It is certified that error appears in the above-indentified patent and that said Letters Patent is hereby corrected as shown below:

Column 10, lines 31-33: please delete the term "pentamethylcyclopentadienyldi-t-butylphosphinomethylethyl" and substitute therefor -- pentamethylcyclopentadienyldi-t-butylphosphidomethylethyl --;

Column 10, line 37: please insert -- 1. -- between "Table" and "An";

Column 10, line 38: please delete the term "dimethylsilyclopentadienyl-t-butylamidodichloro" and substitute therefor -- dimethylsilylcyclopentadienyl-t-butylamidodichloro --;

Column 10, line 60: please delete the term "$R_2$" and substitute therefor -- $R^2$ --;

Column 12, line 50: please delete the term "o-olefin" and substitute therefor -- α-olefin --;

Column 12, line 52: please delete the term "α-olefin" and substitute therefor -- α-olefins --;

Column 12, line 64: please delete the term "10 hour" and substitute therefor -- 10 hours --;

Column 13, line 65: please delete the term "D-BuLi" and substitute therefor -- n-BuLi --;

UNITED STATES PATENT AND TRADEMARK OFFICE
CERTIFICATE OF CORRECTION

PATENT NO. : 5,096,867
DATED : March 17, 1992
INVENTOR(S) : Jo Ann M. Canich

It is certified that error appears in the above-indentified patent and that said Letters Patent is hereby corrected as shown below:

Column 14, line 9: please insert -- purchased from Aldrich Chemical Company or Petrarch -- between "were" and "Systems.";

Column 14, line 33: please delete the formula "$Me_2Si(Me_4HC_5)(HN-st-Bu)$" and substitute therefor -- $Me_2Si(Me_4HC_5)(HN-t-Bu)$ --;

Column 15, line 65: please delete the formula "$Me_2Si(M_3SiC_5H_4)(NH-t-Bu)$" and substitute therefor -- $Me_2Si(Me_3SiC_5H_4)(NH-t-Bu)$ --;

Column 17, line 59: please delete the formula "$Me_4C_5SiMe_2Cl$" and substitute therefor -- $Me_4HC_5SiMe_2Cl$ --;

Column 17, line 62: please delete the formula "$Me_4C_5SiMe_2Cl$" and substitute therefor -- $Me_4HC_5SiMe_2Cl$ --;

Column 17, line 63: please delete the formula "$LiHNC_5H_4-p-n-Bu$" and substitute therefor -- $LiHNC_6H_4-p-n-Bu$ --;

Column 17, line 65: please delete "- 3 hours" and replace with -- ~ 3 hours --;

Column 18, line 1: please delete the formula "$Me_2Si(Me_4C_5H)(HNCl_6H_4-p-t-Bu)$" and substitute therefor -- $Me_2Si(Me_4C_5H)(HNC_6H_4-p-n-Bu)$ --;

UNITED STATES PATENT AND TRADEMARK OFFICE
CERTIFICATE OF CORRECTION

PATENT NO. : 5,096,867
DATED : March 17, 1992
INVENTOR(S) : Jo Ann M. Canich

It is certified that error appears in the above-indentified patent and that said Letters Patent is hereby corrected as shown below:

Column 18, line 1: please delete the formula "$Me_2Si(Me_4C_5H)(HNCl_6H_4$-p-t-Bu)" and substitute therefor -- $Me_2Si(Me_4C_5H)(HNC_6H_4$-n-t-Bu) --;

Column 18, line 4: please delete the word "dilute" and substitute therefor -- diluted --;

Column 18, lines 22-23: please delete the term ".3-/4Et2O" and substitute therefor -- •¾$Et_2O$ --;

Column 18, lines 39-40: please delete the carriage return between "mol)" and "was";

Column 19, line 52: please delete the formula "$Me_2Si(C_5Me_4)(NC_6H_4$-p-n-Bu)$TiCl_2O$" and substitute therefor -- $Me_2Si(C_5Me_4)(NC_6H_4$-p-n-Bu)$TiCl_2$ --;

Column 20, line 38: please delete the formula "$Me_2Si(t$-$Bu_2C_5H_4)(HN$-2,5-t-$Bu_2C_6H_3)$" and substitute therefor -- $Me_2Si(t$-$BuC_5H_4)(HN$-2,5-t-$Bu_2C_6H_3)$ --;

Column 21, line 10: please delete the term "t-BuLi" and substitute therefor -- n-BuLi --;

Column 21, line 16: please delete the space between "Li" and "$_2$";

UNITED STATES PATENT AND TRADEMARK OFFICE
CERTIFICATE OF CORRECTION

PATENT NO. : 5,096,867
DATED : March 17, 1992
INVENTOR(S) : Jo Ann M. Canich

It is certified that error appears in the above-indentified patent and that said Letters Patent is hereby corrected as shown below:

Column 21, lines 51-52: please delete the term "$TiCl_4\ 2Et_2O$" and substitute therefor -- $TiCl_4 \cdot 2Et_2O$ --;

Column 21, lines 67-68: please delete the formula "$Me_2Si(C_5Me_4)(NC_6H_{11})TiCl$" and substitute therefor -- $Me_2Si(C_5Me_4)(NC_6H_{11})TiCl_2$ --;

Column 22, line 6: please delete the term "- 1 hour" and replace with -- ~ 1 hour --;

Column 22, line 25: please delete the term "$TiCl_4\ 2Et_2O$" and substitute therefor -- $TiCl_4 \cdot 2Et_2O$ --;

Column 22, line 59: please delete the term "$Li_2[Me_2Si(C_5Me_4(NPh)]$" and substitute therefor -- $Li_2[Me_2Si(C_5Me_4)(NPh)]$ --;

Column 22, lines 60-61: please delete the term "$TiCl_4\ 2Et_2O$" and substitute therefor -- $TiCl_4 \cdot 2Et_2O$ --;

Column 23, line 66: please delete the term "$TiCl_4\ 2Et_2O$" and substitute therefor -- $TiCl_4 \cdot 2Et_2O$ --;

Column 27, line 52: please delete the term "0.278 m" and substitute therefor -- 0.278 mg --;

UNITED STATES PATENT AND TRADEMARK OFFICE
CERTIFICATE OF CORRECTION

PATENT NO. : 5,096,867
DATED : March 17, 1992
INVENTOR(S) : Jo Ann M. Canich

It is certified that error appears in the above-indentified patent and that said Letters Patent is hereby corrected as shown below:

Column 29, line 29: please delete the term "1.0MAO" and substitute therefor -- 1.0M MAO --;

Column 30, line 21: please delete the number "5.5" and substitute therefor -- 15.5 --;

Column 30, line 51: please delete the number "48,600" and substitute therefor -- 548,600 --;

Column 30, line 63: please delete the word "ethyleme" and substitute therefor -- ethylene --;

Column 32, line 35: please delete the term "1-hexane" and substitute therefor -- 1-hexene --;

Column 33, line 31: please delete the word "Was" and substitute therefor -- was --;

Column 37, line 60: please delete the letter "b" between the words "and" and "1-butene";

Column 38, line 14: please delete the term "i-butene" and substitute therefor -- 1-butene --;

Column 40, line 53: please delete the number "39" and substitute therefor -- 70 --;

UNITED STATES PATENT AND TRADEMARK OFFICE
CERTIFICATE OF CORRECTION

PATENT NO. : 5,096,867
DATED : March 17, 1992
INVENTOR(S) : Jo Ann M. Canich

It is certified that error appears in the above-indentified patent and that said Letters Patent is hereby corrected as shown below:

Columns 41-42, Table 2: please delete the column heading "mmole MAO:TMC (x $10^3$)" and substitute therefor -- molar MAO:TMC (x $10^{-3}$) --;

Columns 41-42, Table 2, Experiment No. 4, fifth column from the left: please delete the number "5.588 x $10^4$" and substitute therefor -- 5.588 x $10^{-4}$ --;

Columns 43-44, Table 2: please delete the column heading "mmole MAO:TMC (x $10^3$)" and substitute therefor -- molar MAO:TMC (x $10^{-3}$) --;

Columns 43-44, Table 2, column headed "EXP. NO.": please delete the number "30" and substitute therefor -- 31 --;

Columns 43-44, Table 2, column headed "EXP. NO.": please delete the number "32" and substitute therefor -- 33 --;

Columns 45-46, Table A: please delete the column heading "mmole MAO:TMC (x $10^3$)" and substitute therefor -- molar MAO:TMC (x $10^{-3}$) --;

Columns 45-46, Table B: please delete the column heading "mmole MAO:TMC (x $10^3$)" and substitute therefor -- molar MAO:TMC (x $10^{-3}$) --;

UNITED STATES PATENT AND TRADEMARK OFFICE
CERTIFICATE OF CORRECTION

PATENT NO.  :   5,096,867
DATED       :   March 17, 1992
INVENTOR(S) :   Jo Ann M. Canich It is certified that error appears in the above-indentified patent and that said Letters Patent is hereby corrected as shown below:

Columns 45-46, Table D, column headed "Catalyst TMC Feal Rate mmole/hr": please delete the word "Feal" in the heading and substitute therefor -- Feed --.

Columns 45-46, Table D, column headed "MW": please delete the number "1.15" associated with Example 63 and substitute therefor -- 38,800 --.

Columns 47-48, Table D, column headed "Catalyst TMC Feal Rate mmole/hr": please delete the word "Feal" in the heading and substitute therefor -- Feed --.

Signed and Sealed this

Twelfth Day of September, 2000

Attest:

Q. TODD DICKINSON

*Attesting Officer*  *Director of Patents and Trademarks*